(12) United States Patent
Kassab et al.

(10) Patent No.: US 8,506,516 B2
(45) Date of Patent: Aug. 13, 2013

(54) DEVICES, SYSTEMS, AND METHODS FOR ACHIEVING MAGNETIC GASTRIC BYPASS

(75) Inventors: Ghassan S. Kassab, Indianapolis, IN (US); Jose A. Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 651 days.

(21) Appl. No.: 12/602,476

(22) PCT Filed: May 29, 2008

(86) PCT No.: PCT/US2008/065140
§ 371 (c)(1),
(2), (4) Date: Jun. 15, 2010

(87) PCT Pub. No.: WO2008/150905
PCT Pub. Date: Dec. 11, 2008

(65) Prior Publication Data
US 2010/0318015 A1  Dec. 16, 2010

Related U.S. Application Data

(60) Provisional application No. 60/940,596, filed on May 29, 2007.

(51) Int. Cl.
*A61F 2/04* (2006.01)
(52) U.S. Cl.
USPC .......................................................... 604/8
(58) Field of Classification Search
None
See application file for complete search history.

(56) References Cited

U.S. PATENT DOCUMENTS

| 6,558,400 | B2* | 5/2003 | Deem et al. .................. 606/151 |
| 7,175,669 | B2* | 2/2007 | Geitz ........................... 623/23.7 |
| 2004/0249459 | A1 | 12/2004 | Ferree |
| 2004/0267291 | A1 | 12/2004 | Byrum et al. |
| 2005/0283107 | A1 | 12/2005 | Kalanovic |
| 2006/0036267 | A1 | 2/2006 | Saadat et al. |
| 2006/0282106 | A1 | 12/2006 | Cole et al. |
| 2007/0032807 | A1 | 2/2007 | Ortiz |

OTHER PUBLICATIONS

PCT/US2008/065140, International Searching Authority, PCT Search Report, dated Oct. 2, 2008.
PCT/US2008/065140, International Searching Authority, Written Opinion, dated Oct. 2, 2008.
PCT/US2007/015238, International Searching Authority, PCT Search Report, dated Aug. 27, 2008.
PCT/US2007/015238, International Searching Authority, Written Opinion, dated Aug. 27, 2008.

* cited by examiner

*Primary Examiner* — Loan Thanh
*Assistant Examiner* — Andrew S Lo
(74) *Attorney, Agent, or Firm* — Reichel IP LLP; Mark C. Reichel; Kevin R. Erdman

(57) ABSTRACT

Devices, systems and methods are disclosed for the treatment of obesity. A magnetic device is provided that enables the creation of a Roux limb without the use of staples or sutures. Additionally, a magnetic device is described for extending the length of the Roux limb such that tension in the stomach and/or the intestines is prevented. Further, a system and method are described for achieving the reversible restriction of gastric capacity and bypass of the duodenum without the use of sutures or staples.

18 Claims, 26 Drawing Sheets

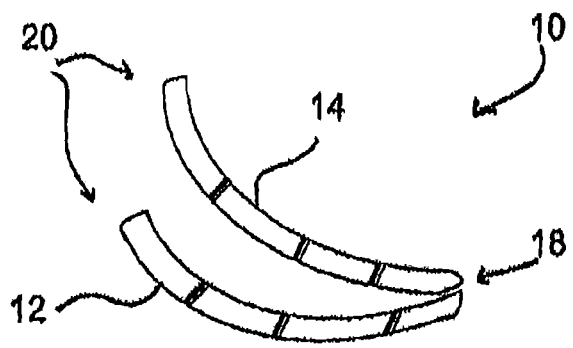
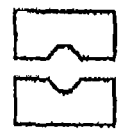
FIG. 2A
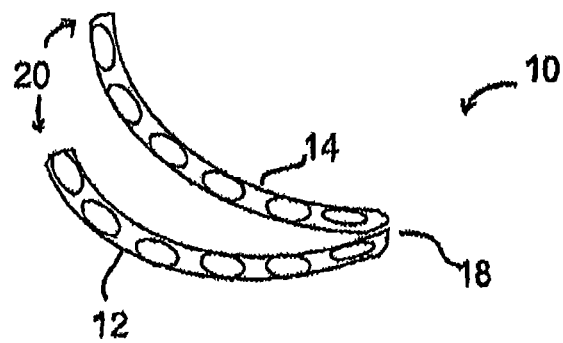
FIG. 2B

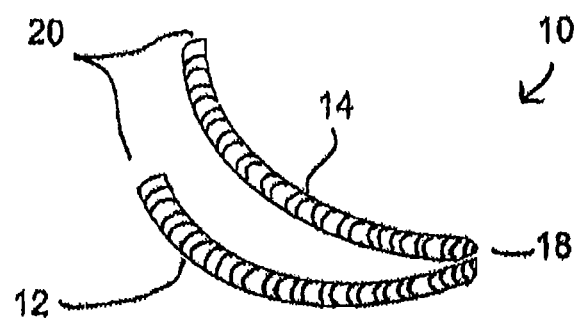
FIG. 2C

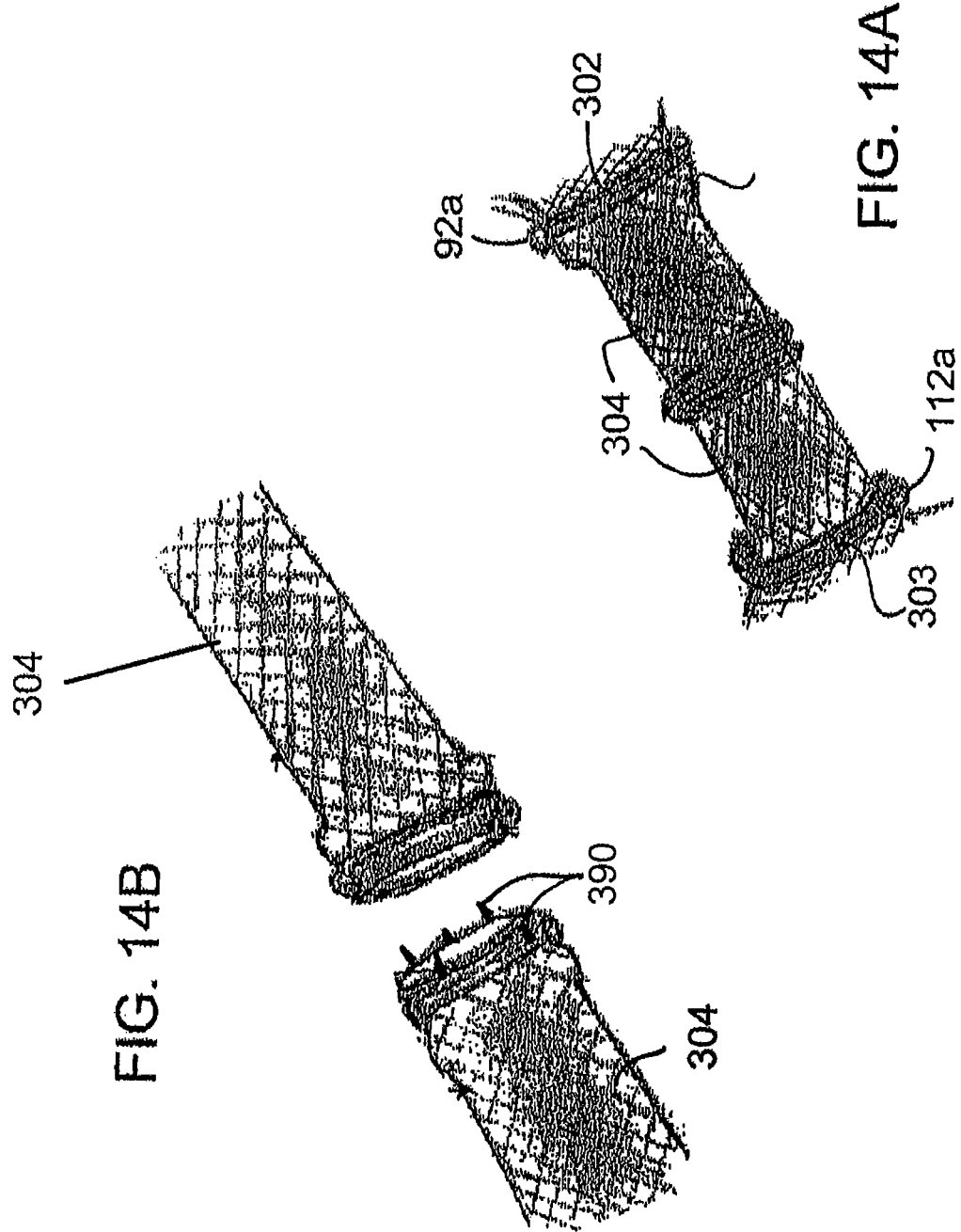

DEVICES, SYSTEMS, AND METHODS FOR ACHIEVING MAGNETIC GASTRIC BYPASS

PRIORITY

This United States Patent Application is a U.S. National Application of, and claims the priority benefit to, International Patent Application Serial No. PCT/US2008/065,140, filed May 29, 2008, which (a) is related to and claims the priority benefit of U.S. Provisional Patent Application Ser. No. 60/940,596, filed May 29, 2007; and (b) is related to and claims the priority benefit of International Patent Application No. PCT/US2007/015,238, filed Jun. 29, 2007, which claims priority to U.S. Provisional Patent Application Ser. No. 60/817,423, filed Jun. 30, 2006. The contents of each of these applications are hereby incorporated by reference in their entirety into this disclosure.

BACKGROUND

Obesity and overweight conditions are a global epidemic and are the most frequent nutritional disorder in Western civilization. Currently, the conditions of "overweight" and "obesity" are classified by body mass index ("BMI"), which is a statistical measure of the weight of a person scaled according to height. From the period of 1988-1994 to the period of 1999-2000, the incidence of overweight adults augmented from 55.9% to 64.5% while the prevalence of obesity increased from 22.9% to 30.5%. The United States especially faces grave public policy concerns with respect to the morbidly obese, i.e. being over 100 pounds above their desirable weight or having one or more serious medical conditions in association with obesity.

In order to treat obesity, conventional procedures involve attempts to either 1) restrict food intake into the body via a restrictive bariatric procedure (a "Restrictive Procedure"), or 2) alter the anatomy of the small intestine or divert the peristalsis of a person's normal food intake past the small intestine to decrease caloric absorption via a malabsorptive bariatric procedure, which is commonly known as a gastric bypass (a "Malabsorptive Procedure"). It is also known to combine the two procedures such that both of the aforementioned techniques are employed jointly.

Each of the abovementioned procedures has advantages and disadvantages. The Malabsorptive Procedures, which entail short circuiting the gastric pouch, have previously been more successful in bringing about sustained weight loss; however, they are typically more difficult to perform, have higher rates of catastrophic post-operative complications, and produce long-term deleterious changes due to the rerouting of the alimentary flow. Restrictive Procedures have encountered more positive results than Malabsorptive Procedures because the Restrictive Procedures tend to be simpler, have fewer major complications, and do not disturb normal digestive tract continuity.

In Malabsorptive Procedures, an intestinal bypass is typically performed. This results in the exclusion of almost all of the small intestine from the digestive tract, such that a lower amount of calories and nutrients can be absorbed. One example of a specific Malabsorptive Procedure is the biliopancreatic diversion ("BPD"). BPD is a procedure in which about three-fourths (¾) of the stomach is removed in order to restrict food intake and decrease stomach acid production. The effect of this procedure is to alter the anatomy of the small intestine via the formation of an alimentary limb. The alimentary limb diverts the passage of food past the first portion of the small intestine, including the duodenum and jejunum, thereby preventing all of the bile and pancreatic juices from digesting the ingested food. As briefly noted above, this process does not come without significant risks.

Conversely, in Restrictive Procedures a passageway is generally constructed from the upper portion of the stomach to the lower portion, thereby preventing the stomach from storing large amounts of food and slowing the passage of food from the esophagus to the small intestine. Conventional Restrictive Procedures rely on the banding and/or stapling of the stomach to create a small pouch on the superior portion of the stomach near the gastroesophageal junction. When first created, this pouch can contain no more than approximately one (1) ounce of food and liquid, but typically later distends to store two (2) to three (3) ounces.

The lower outlet of the created pouch is nondilatable and is typically only one half (½) inch in diameter or smaller. The small pouch receives food and liquid directly from the esophagus and fills quickly. The pouch also diverts the passage of food and liquid to the lower portion of the stomach, thus avoiding storage of food in the stomach itself. Due to the pouch's size and the relatively narrow outlet into the larger stomach, the patient experiences early satiety, which in turn decreases appetite and results in weight loss. Purely Restrictive Procedures for obesity include adjustable gastric banding and vertical banded gastroplasty. These procedures do not affect the digestive process and thus do not result in the risks associated with Malabsorptive Procedures. In addition, Restrictive Procedures are safer than Malabsorptive Procedures and can be performed laparoscopically, thereby further reducing risks of complications.

In all Restrictive Procedures, the volume of the small pouch above the band can increase in size up to ten (10) times after the initial operation. Therefore, the pouch volume during surgery needs to initially be very small. Due to the small pouch size, for the patient to be able to consume sufficient nutrition immediately after the operation, the opening to the stomach initially must be relatively large. Thereafter, as the pouch volume increases, the stoma opening is subsequently reduced to enjoy optimal results of the procedure. In other words, as the gastric pouch size increases, the size of the outlet decreases to further control the amount and rate of digested matter flowing therethrough. Accordingly, the size of the stoma opening should be gradually reduced during the first year after surgery as the gastric pouch increases in size.

One Restrictive Procedure, adjustable gastric binding ("AGB"), provides an adjustment means, thereby enabling minor post-operation adjustments of the size of the stoma opening. In AGB, a band is placed around the superior portion of the stomach to form a small pouch and a narrow passageway to the rest of the stomach. The band itself typically comprises a hollow silicone rubber band having an inflatable cavity. The inflatable cavity of the band is capable of being inflated with a fluid—typically an isotonic salt solution—through a tube that connects the band to an access port, which is typically located subcutaneously so that it may be easily accessed by the patient. Over time, the band may be tightened or loosened to modify the size of the stoma opening by increasing or decreasing the quantity of fluid within the cavity of the band. By adding liquid to the cavity of the band, the band expands radially inward and decreases the size of the stoma opening.

A great disadvantage of AGB, however, is that as a result of the direct manipulation of the bands, the rubber bands forming the gastric pouch tend to slip or wear away. In addition, in the conventional AGB process where the fluid is added to the band cavity by way of an injection into the access port, repeated injections into the same area increases the risk of infection in the area surrounding the access port. In addition, it is uncomfortable for the patient when the necessary post-operation adjustments of the stoma opening are carried out by using a needle to access the port through the skin of the patient.

Similar to AGB, vertical banded gastroplasty ("VBG") is a Restrictive Procedure that utilizes rubber bands as well as staples to create the small stomach pouch. Unlike AGB, however, VBG is not manually adjustable. The VBG procedure involves puncturing the stomach to create a pouch. Like AGB, VBG is prone to slippage and/or band deterioration. Additional complications also may arise with VBG, including staple-line disruption, which can result in stomach content leakage and/or serious infection. Such complications may require prolonged hospitalization with antibiotic treatment and even additional operations. Based on the associated risks, VBG has been classified by the American Medical Association as a "severely dangerous" operation.

Combined operations consisting of Malabsorptive and Restrictive Procedures are the most common bariatric procedures performed today. Such combined procedures restrict both food intake and the amount of calories and nutrients that the body is capable of absorbing. An example of a combined procedure is the Extended (Distal) Roux-en-Y Gastric Bypass ("RYGBP-E") in which a stapling creates a small (approximately 15 to 20 cc) stomach pouch completely separated from the remainder of the stomach. The small intestine is divided just beyond the duodenum (the hollow tube connecting the stomach to the jejunum), and is re-arranged into a Y-configuration to enable outflow of food from the small upper stomach pouch, via a "Roux limb". Accordingly, the small intestine forms the outlet of the newly formed stomach pouch, which empties directly into the lower portion of the jejunum, thus bypassing caloric absorption. The length of either segment of the intestine can be increased to adjust the levels of malabsorption.

As this procedure is conventionally performed, the surgeon must ensure that the stomach and the various portions of the intestine are free from tension when the position of the organs are reconfigured to achieve the bypass. This concern is exemplified when staples are employed to create the anastomoses and/or to create the small stomach pouch as even a slight amount of tension will cause the staples to rip from the tissue. Accordingly, any degree of tension present in the stomach or the intestine as a result of the RYGBP-E procedure presents a high risk that the staples may rip free from the tissue and thereby damage to the underlying organs, inhibit the proper flow of digested matter through the newly configured channels, or both. Accordingly, a considerable amount of time is typically spent during each RYGBP-E procedure to ensure that the stomach and intestine are tension-free.

In addition to the risks associated with tension, other complications may arise. Because the duodenum is bypassed in this procedure, poor absorption of iron and calcium can result in a decreased total body iron concentration and a predisposition to iron deficiency anemia. Additional complications of the RYGBP-E procedure include a condition known as "dumping syndrome". Normally, the pyloric valve at the lower end of the stomach regulates the release of food into the bowel. Dumping syndrome is a condition in which the stomach contents rapidly pass into the small intestine resulting in extremely unpleasant conditions including nausea, weakness, sweating, faintness and, on occasion, diarrhea after eating. Because sugar passes especially rapidly into the bowel, some patients are unable to eat any form of sweets after RYGBP-E surgery. While these complications may be outweighed by the risks associated with obesity, if the procedure is successful and the patient later achieves and maintains a healthy weight, such complications nevertheless remain.

Being obese has many health ramifications. Obesity is an important risk factor for a number of diseases and increases risk factors that heavily predispose for cardiovascular disease. In addition, systemic hypertension, pulmonary hypertension (left ventricular failure, chronic hypoxia), and coronary heart disease all occur with excessively high frequency in obese individuals and may be the source or influence in cardiac structure and function alterations. The risk of sudden cardiac death is also elevated in obese individuals.

Accordingly, a need exists for a safe and effective method of treating obesity. The current Restrictive, Malabsorptive, and combination procedures present a high risk of several complications, including malnutrition, infections, vomiting, and recurrence resulting from band slippage or deterioration. Further, the procedures of the prior art are permanent and cannot be reversed when a healthy weight is achieved. There is therefore a need for a new, reversible technique that minimizes the complications associated with the conventional procedures known in the art.

SUMMARY

Devices, systems and methods are provided for the treatment of obesity without the use of sutures or staples. Certain devices and systems comprise a coupling device for achieving an anastomosis without the use of sutures or staples, and that may be delivered laparoscopically. Such devices comprise a first magnetic component for placement around a stoma in a first tissue and a second magnetic component for placement around a stoma in a second tissue, wherein when the first and second magnetic components are in proximity, the magnetic components are biased to magnetically engage, hold the first and second tissues therebetween, and enable communication between the stoma in the first tissue and the stoma in the second tissue. In at least one example, the stoma in the first tissue can comprise a gastrotomy site in a stomach and the stoma in the second tissue can comprise an enterotomy site in an intestine. Indeed, the coupling device may be employed to form a suture and staple-free anastomosis to bypass the duodenum from digestion.

The first magnetic component of the coupling device may further comprise a first open end comprising, a second open end, and a body extending between the first and second open ends, the body comprising at least one magnet. The first open end may also comprise a first magnetic ring having a perimeter and a plurality of barbs extending radially from the perimeter. In at least one embodiment, the body and the second open end of the first magnetic component are capable of conforming to an exterior of a first organ and the plurality of barbs are configured to puncture a first tissue. For example and without limitation, the first organ may comprise a stomach and the first tissue may comprise gastric tissue.

The second magnetic component of the coupling device may further comprise a first open end, a second open end comprising a joint, a body extending between the first and second open ends and defining a hollow interior, and a stent cover coupled with the joint of the second open end. The first open end may further comprise a second magnetic ring having a perimeter and a plurality of barbs extending from the perimeter, the barbs configured to puncture a second tissue. For example and without limitation, each of the plurality of barbs of the first and second magnetic rings may be comprised in an arrow-head like configuration such that the barbs are capable of retaining tissue thereon. Further, the body of the second magnetic component may comprise a first length and at least one magnet. Additionally, the hollow interior of the body may be configured to receive at least a portion of a second organ therein. For example and without limitation, the hollow interior of the second magnetic component may be configured to receive a portion of a jejunum therein.

The stent cover may further comprise at least one magnetic flap, each of the at least one magnetic flaps comprising a second length, being capable of moving relative to the joint between an extended position and a folded position, and biased to magnetically engage the body of the second magnetic device and at least a portion of the body of the first magnetic device when the at least one magnetic flap is in the folded position. Each of the magnetic flaps may also further comprise at least one flat magnet and/or at least one filament extending therefrom. Such filaments extending from a magnetic flap can be used to assist a user in maneuvering the magnetic flap between the extended and folded positions.

The first length of the body of the second magnetic component is shorter than the second length of the at least one magnetic flap. Accordingly, this facilitates the magnetic engagement between the at least one magnetic flap and the body of the first magnetic component when the at least one magnetic flap is in the folded position. Furthermore, when the first and second magnetic rings are in proximity, the first and second magnetic rings are biased to magnetically engage through the first and second tissues. In at least one embodiment, the first tissue may comprise stomach tissue and the second tissue may comprise jejunal tissue, and it will be understood that the coupling device may be used to connect any types of tissue and/or organs.

The devices may further include a stent for placement between a stoma in a first tissue and a stoma in a second tissue. These stents may comprise a coupling device having a first magnetic component and a second magnetic component, and an elongated body extending between the first magnetic component and the second magnetic components of the coupling device and defining an enclosed interior. Here, the first magnetic component may be capable of magnetically engaging a first member coupled with a stoma in a first tissue and can be configured to receive matter or gas therethrough. Additionally, the second magnetic component may be capable of magnetically engaging a second member coupled with a stoma in a second tissue and configured to receive matter or gas therethrough. In this manner, when the first magnetic component is positioned proximal to the first member and the second magnetic component is positioned proximal to the second member, an elongated anastomosis is formed between the stoma in the first tissue and the stoma in the second tissue. For example and without limitation, the stoma in the first tissue can comprise a gastrotomy site on a stomach and/or the stoma in the second tissue can comprise an enterotomy site on an intestine.

The first magnetic component of the stent may further comprise a similar configuration to the first magnetic components described in connection with the above-referenced coupling device. In addition, the second magnetic component of the stent may further comprise a similar configuration to the second magnetic components described in connection with the above-referenced coupling device. For example, the first magnetic component of the coupling device may further comprise a first open end, a second open end, and a body extending between the first open end and the second open end. The body of the first magnetic component may comprise at least one magnet and the first open end may further comprise a first magnetic ring capable of magnetically engaging the first member coupled with the stoma in the first tissue. The second magnetic component of the coupling device may comprise a first open end, a second open end comprising a joint, a body extending between the first and second open ends and defining a hollow interior, and a stent cover coupled with the joint of the second open end. In this embodiment, the body may comprise a first length and at least one magnet. Further, the first open end may comprise a second magnetic ring capable of magnetically engaging the second member coupled with the stoma in the second tissue. In addition, the stent cover may comprise at least one magnetic flap, wherein each of the magnetic flaps comprises a second length that is longer than the first length of the body. Further, each of the magnetic flaps may be capable of moving relative to the joint between an extended position and a folded position, and may be magnetically biased to engage the body of the second magnetic component when the at least one magnetic flap is in the folded position.

In another embodiment, the stent may comprise a first open end, a second open end, and a body that extends between the first and second open ends and defines a hollow interior. Here, the first open end is configured for attachment to a stoma in a small gastric pouch such that the interior of the stent is in communication with the interior of the small gastric pouch. Further, the second open end is configured for attachment to a stoma in a jejunum such that the interior of the stent is in communication with the interior of the jejunum. In this manner, the stent is capable of providing an elongated anastomosis between the small gastric pouch and the jejunum such that the duodenum is bypassed from digestion.

Systems are also provided for preventing tension in tissues connected through an anastomosis, a complication that is particularly common in connection with gastric bypass procedures. Such systems comprise the various components discussed above, including a stent for placement between a stoma in a first tissue and a stoma in a second tissue, a first coupling device for placement between the first tissue and the interior of the stent, and a second coupling device for placement between the second tissue and the interior of the stent.

Further, systems are provided for reducing the medically effective volume of a stomach and bypassing the duodenum from the digestion of ingested matter. Such systems comprise an apparatus for restricting the medically effective volume of a stomach and a coupling device for bypassing the duodenum. Specifically, embodiments of the apparatus for restricting the medically effective volume of a stomach comprise an elongated magnetic bar for placement around a gastric wall. This elongated magnetic bar may be biased such that when it is applied around the gastric wall, it creates a first stomach portion for the primary digestion of food and a second residual stomach portion. The coupling device employed with the system may comprise any of the various embodiments of the coupling devices previously described. Accordingly, once the apparatus for restricting the medically effective volume of a stomach has been applied to a stomach, the coupling device is capable of forming an anastomosis between the jejunum and the small gastric pouch to reroute ingested matter therethrough and, thus, bypass absorption within the duodenum.

Methods are also provided for achieving the reversible restriction of gastric capacity and bypass of the duodenum without the use of sutures or staples. The method may comprise the steps of providing the apparatus comprising a magnetic bar for restricting the medically effective volume of a stomach, placing the magnetic bar around the gastric wall to result in a first stomach portion and a second stomach portion, providing a first coupling device comprising first and second magnetic components for bypassing the duodenum from the digestion of ingested matter, dividing a small intestine between the duodenum and the jejunum such that a stoma is formed on the jejunum and a stoma is formed on the duodenum, attaching the first magnetic component around the stoma on the first stomach portion; attaching the second magnetic component around the stoma on the jejunum; magnetically engaging the first magnetic component and the second magnetic component such that the stoma on the first stomach portion and the stoma on the jejunum are in communication with each other, and such that the stoma on the first stomach portion and the stoma. In at least one embodiment of this method, the first stomach portion created through the use of the magnetic bar comprises an upper portion of the stomach and the second stomach portion comprises a lower portion of the stomach. Further, the second stomach portion is not in communication with the first stomach portion such that ingested matter is not allowed to exit the stomach through the duodenum.

In addition to the above-listed steps, the method may further comprise the steps of forming a stoma on a distal portion of the jejunum, providing a second coupling device comprising third and fourth magnetic components for coupling the duodenum with a distal portion of the jejunum, magnetically engaging the third component and the fourth component such that an anastomosis is formed between the stoma on the duodenum and the stoma on the distal portion of the jejunum. In this manner, the biliopancreatic process is kept intact as the digestive juices from the bypassed stomach, pancreas, and liver are allowed to flow through the duodenum and enter the jejunum or ileum to aid in the digestion of food, but the ability of the digestive tract to absorb fat is significantly reduced as the digested matter bypasses the duodenum.

Methods for reversing a treatment for obesity are also described, with certain embodiments comprising the steps of providing a stomach divided into a first stomach portion and a second stomach portion by a magnetic bar biased to create the first stomach portion and the second stomach portion; providing an intestinal tract that has been rerouted such that a jejunum receives ingested food through a gastrotomy site in the gastric wall and a duodenum empties into a distal portion of the jejunum through an enterotomy site in the jejunal wall such that the duodenum is bypassed from the digestion of ingested matter; removing the magnetic bar from the stomach such that the stomach is allowed to revert to the proper anatomical configuration; and occluding the gastrotomy site in the gastric wall such that ingested matter is prevented from flowing therethrough.

BRIEF DESCRIPTION OF THE DRAWINGS

FIGS. 2A-2C show side views of various configurations of a gastric remodeling device comprising a series of discontinuous magnets.

FIGS. 14A and 14B show a stent prosthesis comprising more than one component.

DETAILED DESCRIPTION

Figure 1A:
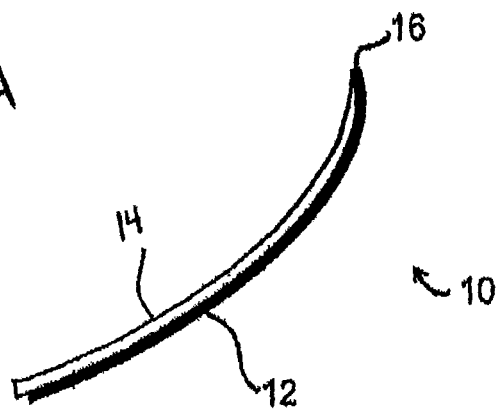
FIG. 1A shows a side view of a gastric remodeling device in a closed position.

Reference will now be made to the embodiments illustrated in the drawings and specific language will be used to describe the same. It will nevertheless be understood that no limitation of scope is intended by the description of these embodiments.

The RYGBP-E procedure generally consists of two separate phases: dividing the stomach into two unequal portions (a smaller upper and a larger, lower gastric pouch), and connecting the jejunum directly to the pouch of the upper stomach. This re-routed segment of the small intestine (i.e. the "Roux loop") functions to carry food from the upper pouch to the remainder of the intestines where the food is digested. The isolated lower stomach and the duodenum are reconnected to a distal portion of the jejunum. In this manner, the biliopancreatic process is kept intact as the digestive juices from the bypassed stomach, pancreas, and liver are allowed to enter the jejunum or ileum to aid in the digestion of food, but the ability of the digestive tract to absorb fat is significantly reduced as the digested matter bypasses the duodenum.

Figure 1B:
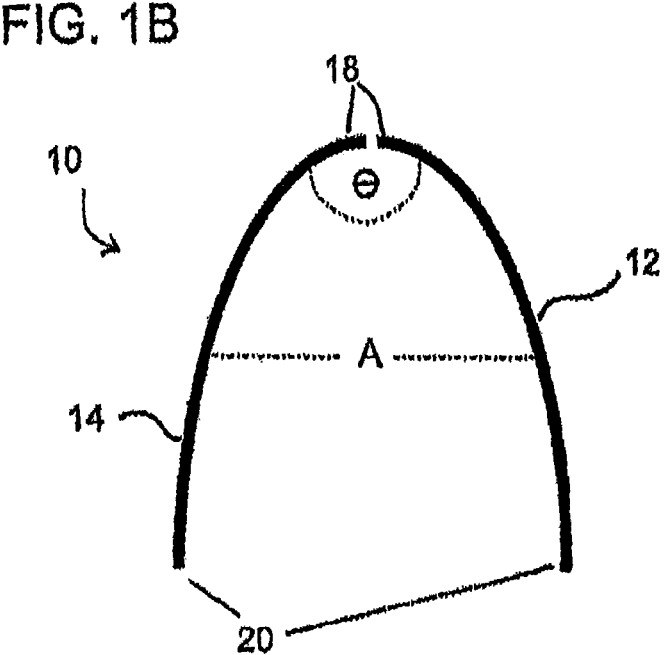
FIG. 1B shows a side view of the gastric remodeling device shown in FIG. 1A in an open position.

International Application Number PCT/US2007/015238 to Kassab et al., which is incorporated herein by reference in its entirety, pertains to an apparatus and method for performing a reversible restriction of a stomach without the use of staples or sutures. FIGS. 1A and 1B show a gastric remodeling device 10 for dividing a stomach into two portions. As will be described in more detail herein, the gastric remodeling device 10 uses magnetic force to compress the anterior and posterior walls of a stomach such that a small gastric pouch is formed (see FIGS. 3A-3C). Accordingly, the gastric remodeling device 10 does not require sutures or staples that could lead to dehiscence (e.g., the opening of the suture site) or fistula (e.g., an abnormal connection between organs or intestines), both of which can cause the production of a significant amount of regurgitation and vomiting.

In FIGS. 1A-2C, several examples of the gastric remodeling device 10 are shown. Referring to FIGS. 1A and 1B, the gastric remodeling device 10 comprises a first magnetic bar 12 and a second magnetic bar 14. Each of the magnetic bars 12, 14 comprise a proximal end 18 and a distal end 20. The first and second magnetic bars 12, 14 may be comprised of any permanent magnet material known in the art and may be flexible, semi-flexible, or articulated. For example, the first and second magnetic bars 12, 14 may each comprise a thin, smooth, ferromagnetic bar.

Alternatively, the first and second magnetic bars 12, 14 may each comprise a series of discontinuous magnets arranged such that the magnets form a continuous and flexible ferromagnetic band. This flexible ferromagnetic band may be enclosed in a laminated configuration of silicone, poly(tetrafluoroethylene) ("PTFE"), small intestine submucosa ("SIS"), any other biologically compatible biomaterial, or a combination of such materials, such that the multiple magnets maintain their band-like configuration.

As shown in FIGS. 2A-2C, each of the magnetic components that form the continuous band may comprise a rectangular, oval, or crescent configuration. It will be understood that the individual magnetic components themselves may comprise any configuration so long as the magnetic components can be coupled together to form a ferromagnetic band. The use of the magnetic components in the composition of the magnetic bars 12, 14 can have the effect of increasing the strength of the magnetic field. Accordingly, this increased magnetic field can be used to further ensure that the stomach tissue disposed between the first and second magnetic bars 12, 14 is securely retained. For example, the rectangular, oval or crescent shapes demonstrate different configurations of north-south dipoles that exert magnetic force in a direction perpendicular to the plane of the stomach tissue. In this manner, the increased magnetic field can provide additional mechanical support to the stomach tissue disposed between the two magnetic bars 12, 14.

In another embodiment, the first magnetic bar 12 and the second magnetic bar 14 each comprise a series of magnets having alternating polarities. For example, the first magnetic bar 12 may comprise a set of three magnets aligned in a specific order of polarity. The second magnetic bar 14 may also comprise a set of three magnets having the opposite order of polarity. In this manner, when the first and second magnetic bars 12, 14 are inserted into the body cavity, laparoscopically or otherwise, the first magnetic bar 12 and the second magnetic bar 14 can only magnetically engage in the proper configuration, thereby facilitating the proper application of the gastric remodeling device 10 to the stomach 25 and simplifying the procedure.

Referring back to the configuration of the first and second bars 12, 14 generally, the first and second magnetic bars 12, 14 may comprise any shape so long as both of the first and second magnetic bars 12, 14 easily conform to a side of a stomach. For example, both the first magnetic bar 12 and the second magnetic bar 14 may each comprise an identical arc-like shape and be disposed in a mating, mirror-image relationship to each other. The first magnetic bar 12 and the second magnetic bar 14 are polarized such that the first magnetic bar 12 and the second magnetic bar 14 are biased towards each other. Due to the matching configuration and the bias between the first magnetic bar 12 and the second magnetic bar 14, the first and second magnetic bars 12, 14 are capable of magnetically engaging each other along their entire lengths. When the first and second magnetic bars 12, 14 magnetically engage, the two magnetic bars 12, 14 form a single unit that is magnetically secured to any tissue disposed therebetween.

Now referring back to FIGS. 1A and 1B, the proximal end 18 of the first magnetic bar 12 magnetically and mechanically engages the proximal end 18 of the second magnetic bar 14. Further, the two magnetic bars 12, 14 are hingedly coupled at their proximal ends 18 and together define an apex 16, an angle θ, and an interior space. The interior space comprises a width A. Merely by way of example, and without any intended limitation, when the first and second magnetic bars 12, 14 are magnetically coupled at their proximal ends 18, the gastric remodeling device 10 may comprise a V-shape configuration. The value of the angle θ formed by the engagement of the proximal ends 18 of the first and second magnetic bars 12, 14 is directly proportionate to the width A of the interior space. Accordingly, when the angle θ increases in value, the width A correspondingly increases. Likewise, as the value of angle θ decreases, the width A decreases. When the first and second magnetic bars 12, 14 are fully engaged, the value of width A equals zero and the first magnetic bar 12 and the second magnetic bar 14 are mechanically engaged along their entire lengths. Accordingly, by altering the value of the angle θ, the gastric remodeling device 10 can move between an "open" and "closed" position.

It will be understood that while the gastric remodeling device 10 has been described herein as comprising first and second magnetic bars 12, 14, the gastric remodeling device 10 may alternatively comprise a single magnetic bar (not shown). In this embodiment, the single magnetic bar may be any ferromagnetic material known in the art, so long as the material comprises some degree of flexibility such that the magnetic bar can be folded to form an apex (similar to the apex 16 shown in FIG. 1A). This single magnetic bar may be inserted into the body cavity through a catheter and subsequently bent into an anterior portion and a posterior portion. Thereafter, the magnetic bar can be positioned on and interact with the stomach 25 in a fashion similar to that described with respect to the first and second magnetic devices 12, 14.

Still further, a nonmagnetic mechanical device can be used in place of the first and second magnetic bars 12, 14 to form the small gastric pouch proximal to the fundus 32 of the stomach 25. It will be recognized that any number of prior art mechanical devices may be employed in forming the small gastric pouch 11, so long as the mechanical device is capable of spanning from the superior surface of the stomach 25 to the inferior surface of the stomach 25 and securely compressing the stomach 25 into two independent portions. Such prior art mechanical devices include, for example, the banding device with a locking mechanism as disclosed in U.S. Pat. No. 5,449,368 to Kuzmak or a ratcheted wire device as disclosed in U.S. Pat. No. 6,558,400 to Deem et al.

Figure 3A:
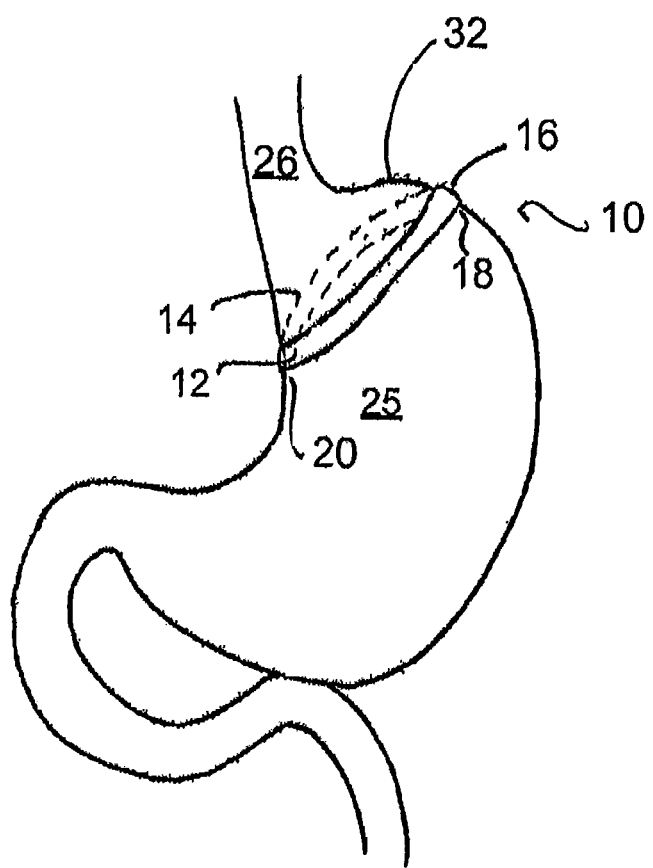
FIG. 3A shows a side view of the gastric remodeling device shown in FIG. 1A applied to a stomach in an open position.
Figure 3B:
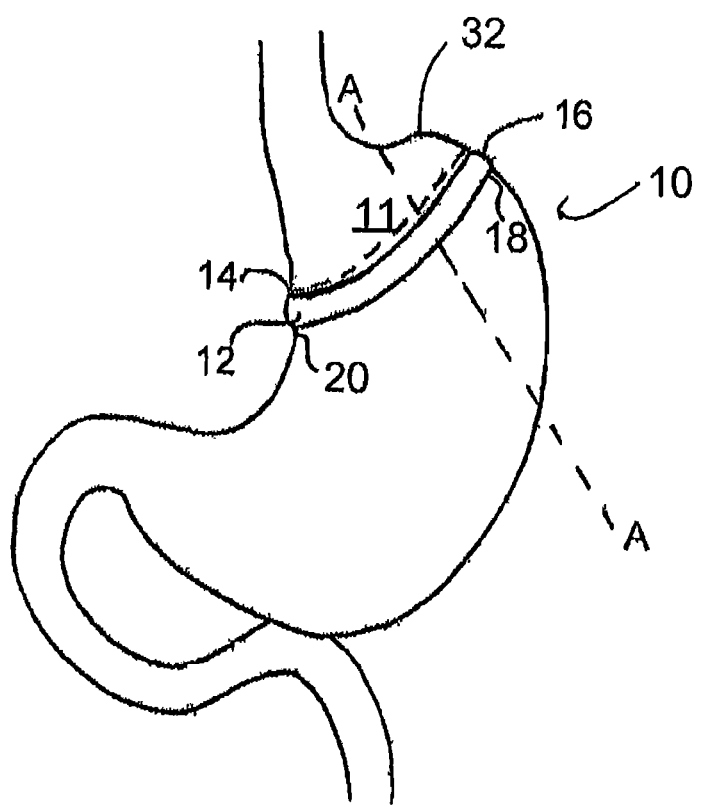
FIG. 3B shows a side view of the gastric remodeling device shown in FIG. 1A applied to a stomach in a closed position.
Figure 3C:
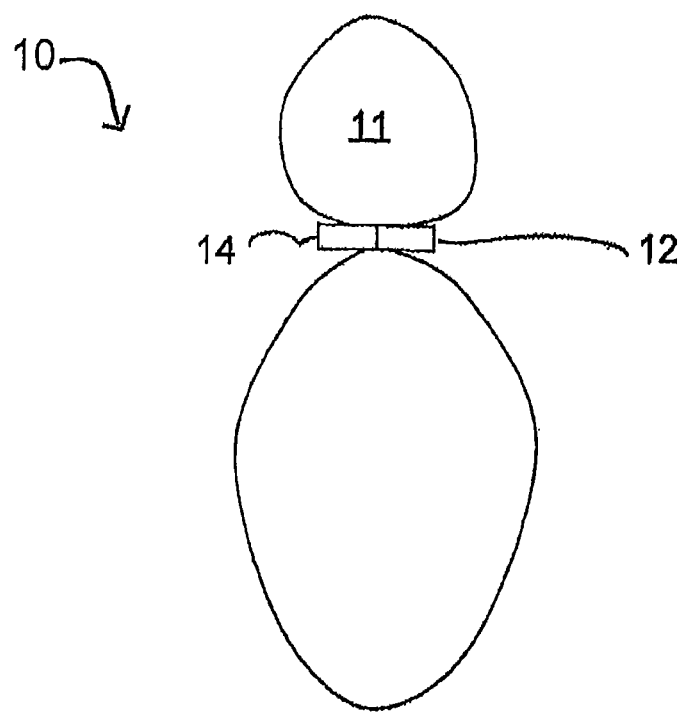
FIG. 3C shows a cross-sectional view of the gastric remodeling device shown in FIG. 3B taken along line A-A.

In operation, the gastric remodeling device 10 is applied to a stomach 25 as shown in FIGS. 3A, 3B, and 3C. FIG. 3A illustrates the open configuration of the gastric remodeling device 10 as the first and second bars 12, 14 are initially applied around the anterior and posterior walls of the stomach (i.e. the angle θ comprises a larger value and the stomach 25 is not constricted, or minimally constricted, by the first and second magnetic bars 12, 14). Specifically, the first magnetic bar 12 is positioned adjacent to the anterior wall of the stomach 25 and the second magnetic bar 14 is positioned adjacent to the posterior wall of the stomach 25. The apex 16 of the gastric remodeling device 10 is positioned proximal to the fundus 32 of the stomach 25 and the gastroesophageal junction 26. Further, the distal ends 20 of the first and second magnetic bars 12, 14 are positioned adjacent to the lesser curvature of the stomach 25, such that the magnetic bars 12, 14 traverse the longitudinal axis of the stomach 25 and the direction of the anatomical flow of matter through the stomach 25. It will be understood that the open position is not limited to when the stomach 25 is not constricted at all by the gastric remodeling device 10, but that the open position may comprise varying degrees of "openness".

FIGS. 3B and 3C illustrate two views of the gastric remodeling device 10 in its closed configuration as the device is applied to the stomach 25 (i.e. the angle θ comprises a smaller value and the stomach 25 is constricted by the first and second magnetic bars 12, 14). The first magnetic bar 12 and the second magnetic bar 14 are capable of magnetically engaging one another through the stomach tissue 25, thereby pinching off a section of the stomach 25. Accordingly, when the first magnetic bar 12 and the second magnetic bar 14 are positioned in the closed configuration on the stomach 25, the stomach 25 is divided into two portions without the use of sutures or staples—one small gastric pouch 11 comprising the upper stomach and one larger stomach portion comprising the lower stomach. It will be appreciated that the "closed" position is not limited to when the angle θ equals zero, but that the closed position may comprise varying degrees of compression.

In general, when the gastric remodeling device 10 is in the open position, a larger volume of the stomach is available for use, as opposed to solely the small gastric pouch 11 when the gastric remodeling device 10 is in the closed position. Because the gastric remodeling device 10 simply holds the anterior and posterior walls of the stomach 25 together and does not puncture the tissue itself, the normal digestive movement of the stomach 25 can be accommodated and the procedure can be easily reversed such that a larger volume of the stomach is available for use. Some leakage will occur from the small gastric pouch 11 into the lower stomach portion; however, due to the magnetic force between the first and second magnetic bars 12, 14, such leakage will be nevertheless incidental. Further, due to the configuration of the small gastric pouch 11, the food and liquid held therein is more inclined to flow through the anastomosis produced in the second phase of the RYGBP-E procedure. Accordingly, the gastric remodeling device 10 prevents digested matter from flowing through the normal course of digestion and thereby produces malabsorptive effects. Furthermore, the small gastric pouch 11 significantly limits the amount of food that the patient can consume at one time and the patient experiences satiety relatively quickly.

As previously described, the RYGBP-E procedure comprises two phases. The first phase of the procedure entails using the gastric remodeling device 10 to create the small gastric pouch 11 and the lower stomach portion as previously described. The second phase of the RYGBP-E procedure entails diverting the food and liquid received by the small gastric pouch 11 around the proximal portion of the intestine (i.e. the duodenum), and thus achieving malabsorption. In order to achieve this modification in the normal route of digestion, a stoma must be created in the gastric wall and the intestines. As used herein, the term "stoma" refers to an artificial opening between two hollow organs, or between one hollow organ and the outside of the body, constructed to permit the passage of body fluids or waste products. Examples of stomas include a gastrotomy site (a stoma in the wall of a stomach) and an enterotomy site (a stoma in the wall of an intestine).

As described herein, and as illustrated in FIGS. 4A-10, the second phase may be achieved without the use of sutures or staples by using a coupling device 100 to form an anastomosis between the small gastric pouch 11 and the jejunum 13. Using the coupling device 100 to create the gastric-jejuno anastomosis in lieu of conventional methods and devices decreases the amount of anastomotic tension present around the anastomosis as well as the incidence of intestinal leakage. Further, the coupling device 100 enables a clinician to perform a sustainable gastric-jejuno anastomosis laparoscopically, without the disadvantages typically associated with suture and staple-based methods. For example, using the coupling device 100 to create an anastomosis between the small gastric pouch 11 and the jejunum 13 eliminates the risk that the patient will experience bleeding incident to the use of staples or staple line dehiscence, and also substantially reduces the risks of anastomotic stricture and kinking of the bowel at the anastomotic site.

Figure 4A:
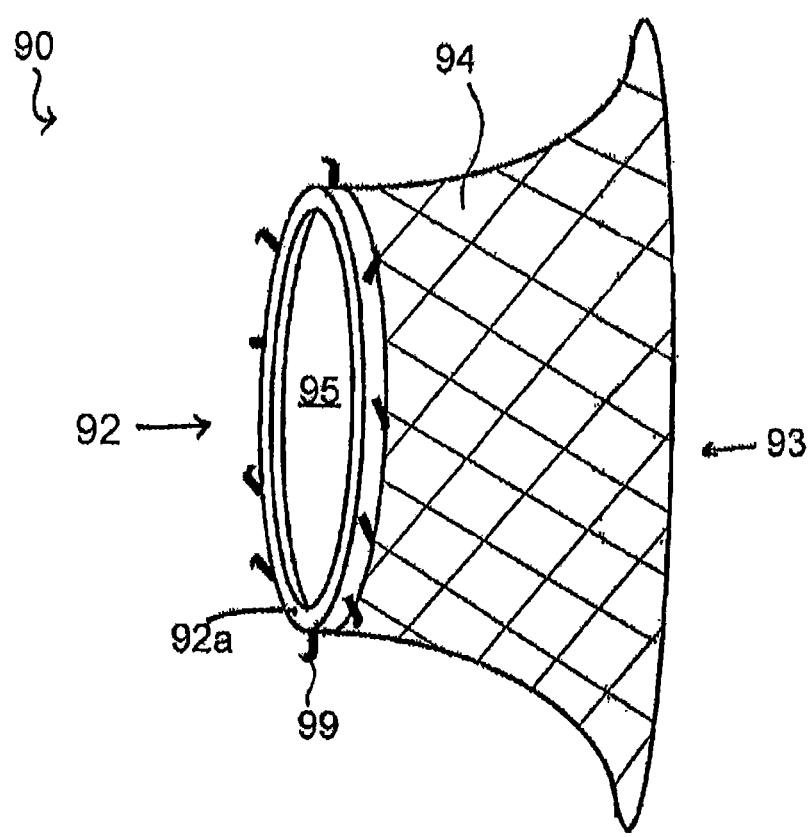
FIG. 4A shows a side view of a gastric component of a coupling device.
Figure 4B:
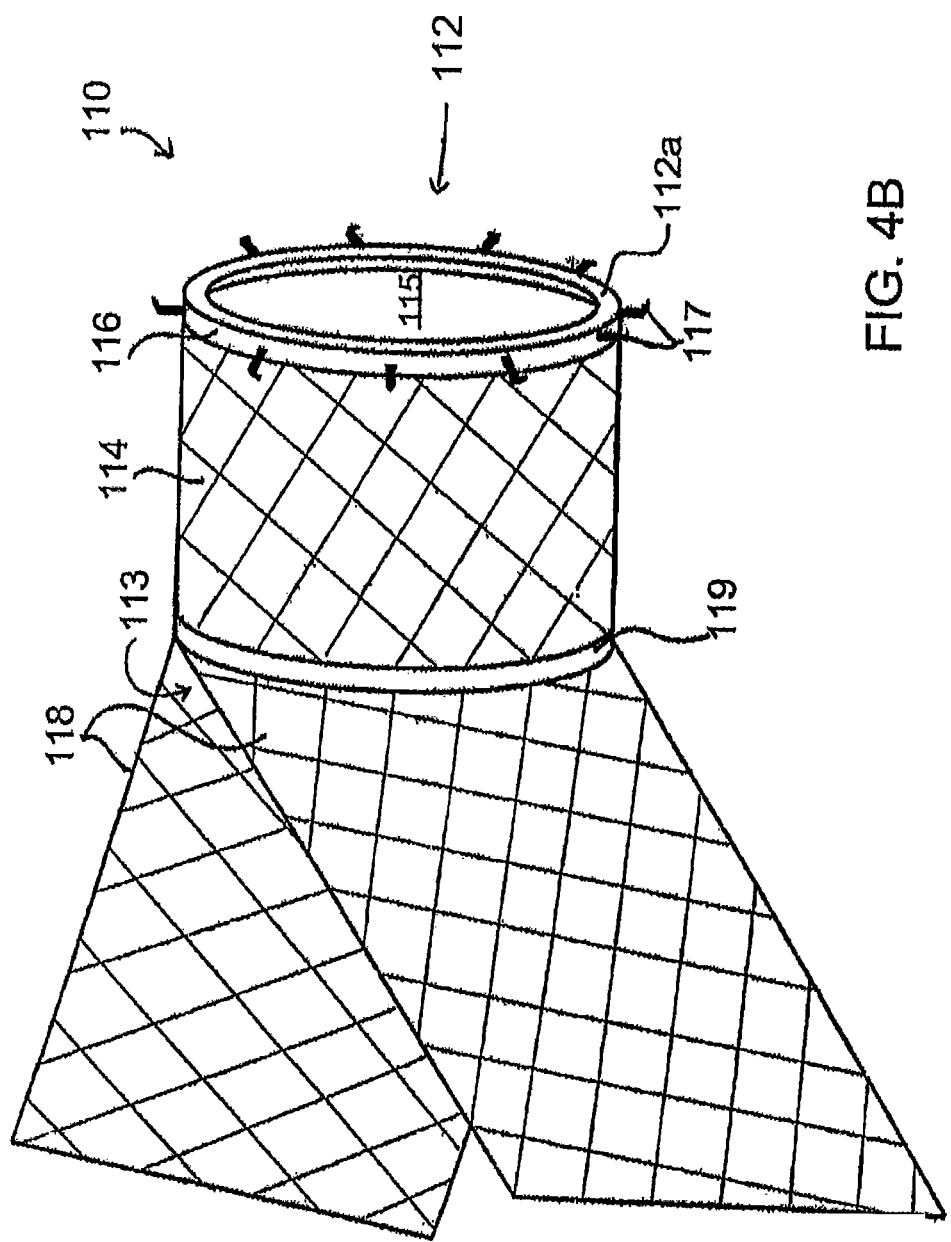
FIG. 4B shows a side view of an intestinal component of a coupling device.

FIGS. 4A and 4B show the components of at least one embodiment of the coupling device 100. In this embodiment, the coupling device 100 comprises a gastric component 90 (see FIG. 4A) and an intestinal component 110 (see FIG. 4B), both of which are capable of laparoscopic insertion into a body cavity. The gastric component 90 comprises a conical shaped magnetic stent having a first open end 92, a second open end 93, a body 94, and a hollow interior 95 that extends between the first open end 92 to the second open end 93. The gastric component 90 is configured to be applied over a gastrotomy site formed in the wall of the small gastric pouch 11. As will be described in more detail herein, the gastric component forms a magnetic base on the small gastric pouch 11 to which the intestinal component 110 can magnetically engage.

The first open end 92 of the gastric component 90 comprises a magnetic ring 92a having a perimeter 96 and a plurality of barbs 99 extending radially therefrom. The magnetic ring 92a is comprised of any ferromagnetic material known in the art so long as the material is capable of magnetically engaging a magnet having the opposite polarity through a tissue. The magnetic ring 92a may be configured in any shape so long as the magnetic ring 92a is capable of substantially surrounding the gastrotomy 60 when the gastric component 90 is applied to the exterior surface of the small gastric pouch 11. For example, in at least one embodiment, the specific configuration of the magnetic ring 92a is selected based on the size and shape of the gastrotomy 60 and/or the particular indications of the patient. In addition, the magnetic ring 92a may be flexible, semi-flexible or articulated.

The body 94 of the gastric component 90 comprises a flexible material having a conical configuration and extends between the first open end 92 and the second open end 93 of the gastric component 90. The body 94 may be comprised of silicone, PTFE, SIS, any other biologically compatible biomaterial, or a combination of such materials. The diameter of the second open end 93 is greater than the diameter of the first open end 92 such that the body 94 comprises a skirt-like shape that is capable of conforming to the curved and/or irregular surface of the small gastric pouch 11. Further, the body 94 of the gastric component 90 comprises at least one magnet disposed therein. For example, the body 94 may comprise a plurality of magnets arranged in a mesh-like configuration. Alternatively, the body 94 may comprise two or more magnets positioned on opposite sides of the body 94 and extending between the first open end 92 and the second open end 93.

Figure 5A:
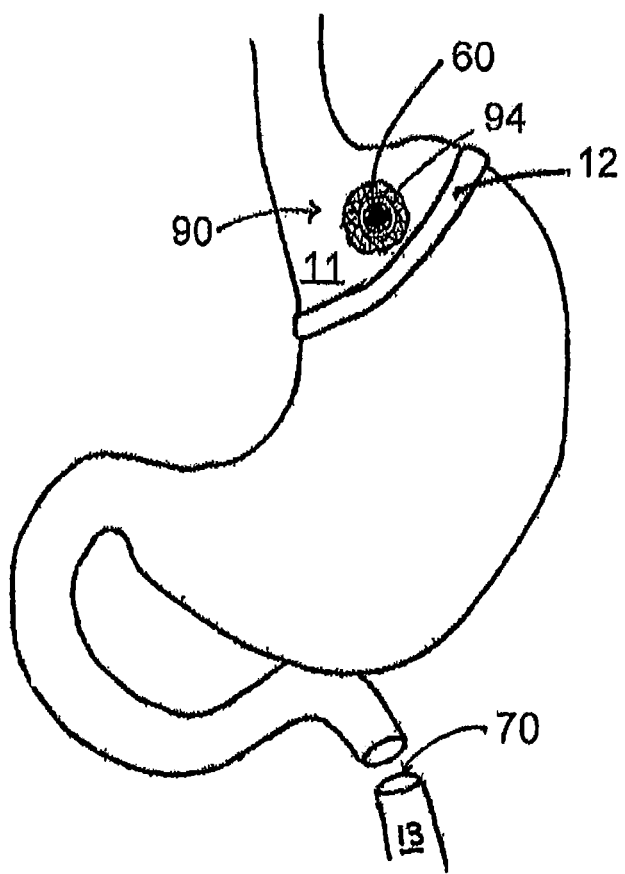
FIG. 5A shows a side view of a stomach comprising the gastric component shown in FIG. 4A applied over a gastrotomy site.
Figure 5B:
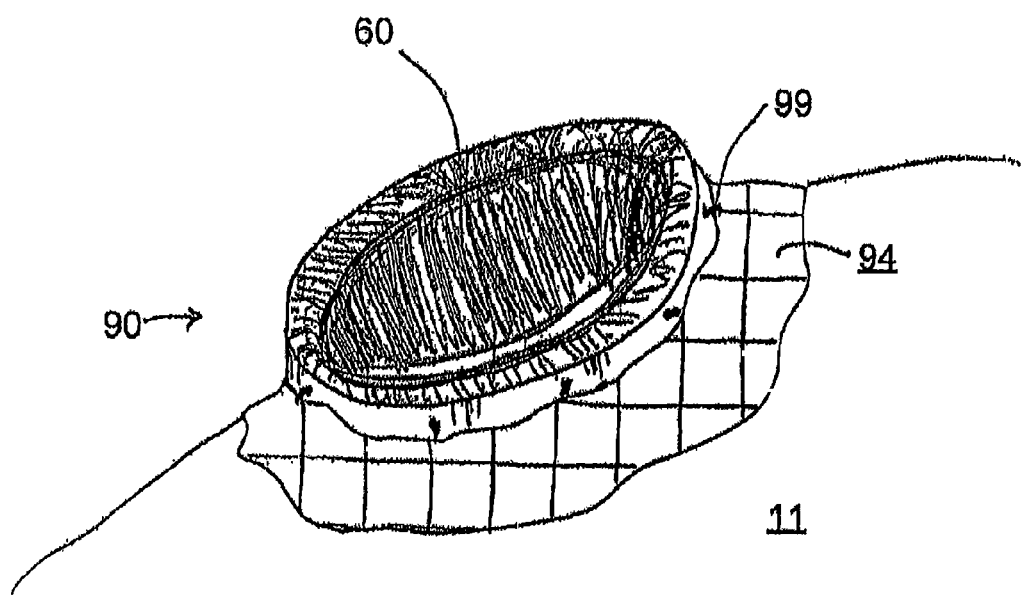
FIG. 5B shows a perspective view of the gastric component shown in FIG. 5A.
Figure 5C:
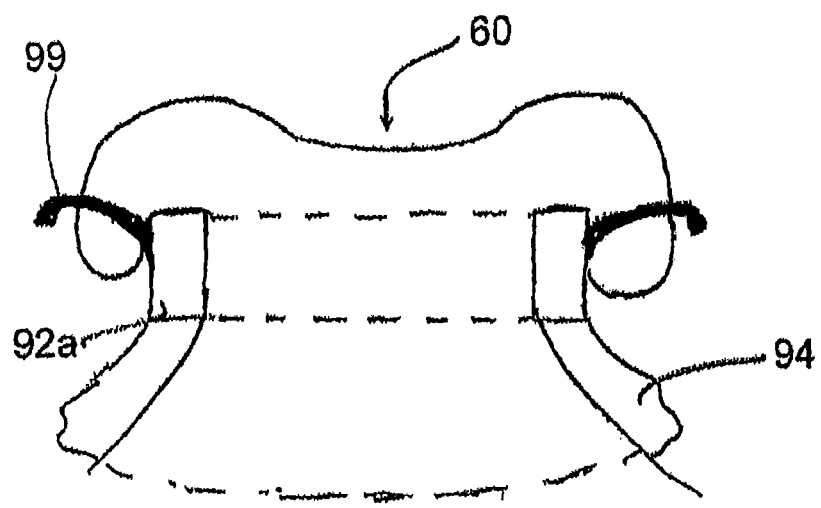
FIG. 5C shows a cross-sectional view of the gastric component shown in FIG. 5A.

FIGS. 5A-5C show the gastric component 90 applied to the gastrotomy site 60 in the wall of the small gastric pouch 11. Specifically, the interior 95 of the gastric component 90 is positioned over the gastrotomy site 60 such that the body 94 expands around the gastrotomy site 60 to conform to the exterior of the stomach 25 and the interior 95 is in communication with the interior of the small gastric pouch 11. To secure the gastric component in place, the edges of tissue surrounding the gastrotomy site 60 are pulled through the interior 95 of the gastric component 90, over the magnetic ring 92a, and attached to the plurality of barbs 99 extending from the magnetic ring's 92a perimeter 96. In this manner, the barbs 99 secure the gastric component 90 to the exterior wall of the small gastric pouch 11 and maintain the gastric component 90 in the proper location around the gastrotomy site 60.

Figure 5D:
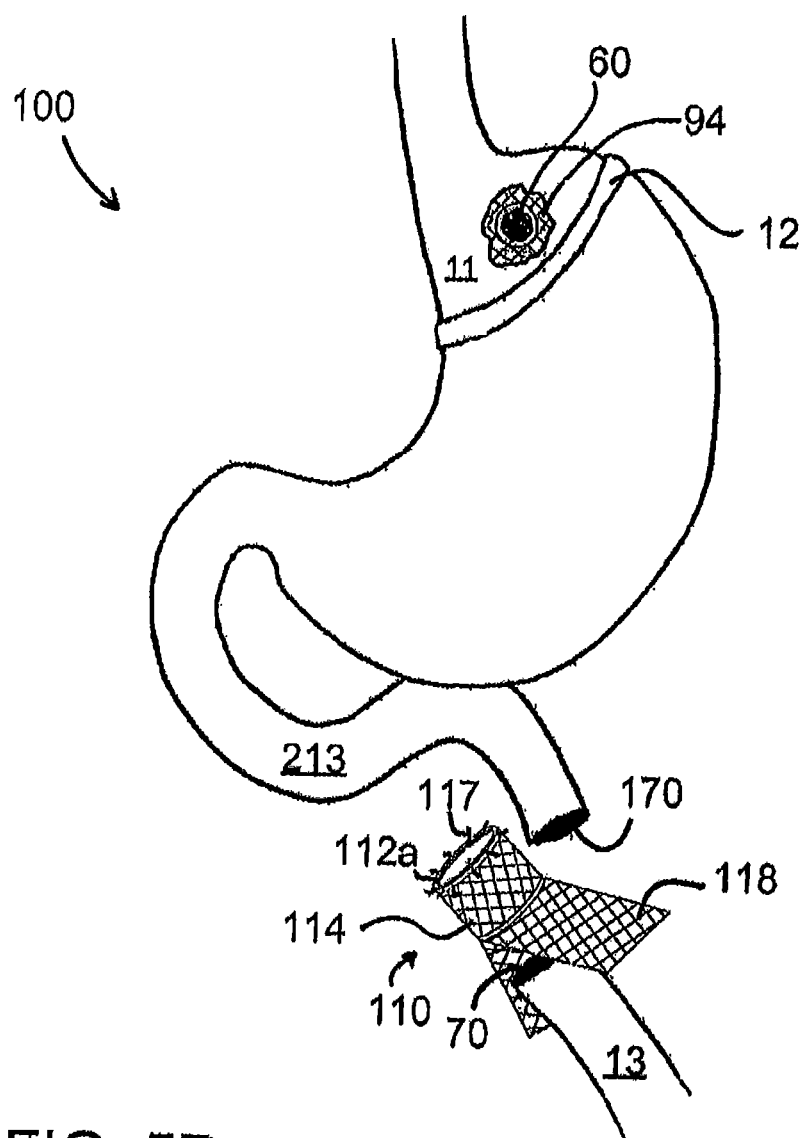
FIG. 5D shows a side view side view of the stomach of FIG. 5A further comprising the intestinal component of FIG. 4B partially applied over a jejunum.

Now referring back to FIG. 4B, a perspective view of the intestinal component 110 is shown. Further, FIG. 5D illustrates the intestinal component 110 in the process of being applied to an enterotomy site 70 in the jejunum 13. Similar to the gastric component 90, the intestinal component 110 comprises a magnetic stent having a first open end 112, a second open end 113, a body 114, and a hollow interior 115 that extends between the first open end 112 and the second open end 113. However, unlike the gastric component 90, the intestinal component 110 further comprises a hemi-stent cover 118 and a crease ring 119. The intestinal component 110 is configured to receive a portion of the small intestine—in particular, the jejunum 13—within the body 114 of the intestinal component 110. Further, the first open end 112 of the intestinal component 110 is designed to couple with the intestine at a location proximal to an enterotomy site 70.

The body 114 of the intestinal component 110 comprises an elongated tube extending between the first open end 112 and the second open end 113. The body 114 may be flexible and, in at least one embodiment, comprises PTFE. Further, the body 114 may comprise any length and, in at least one application, the length of the body 114 is dependent on the particular indications of the patient. Furthermore, the body 114 of the intestinal component 110 comprises at least one magnet. The body 114 may comprise a plurality of magnets arranged in a mesh-like configuration. Alternatively, the body 114 may comprise two or more magnets extending between the first open end 112 and the second open end 113 of the intestinal component 110 and distributed in an evenly spaced manner around the exterior of the body 114.

The second open end 113 of the intestinal component 110 comprises a crease ring 119. The crease ring 119 may comprise PTFE or any other material that allows the hemi-stent cover 118 described below to fold over the area. For example, the crease ring 119 may comprise polyurethane or plastic and is often comprised of the same material as the body 114. The crease ring 119 functions to anchor the second open end 113 of the intestinal component 110 in place when the intestinal component 110 is applied proximally to an enterotomy on a jejunum 13 and the hemi-stent cover 118 is applied thereover.

The hemi-stent cover 118 is coupled with crease ring 119 along the perimeter of the second open end 113 of the intestinal component 110 and extends distally therefrom. The hemi-stent cover 118 comprises at least two magnetic flaps, each of the magnetic flaps having a length greater than the length of the body 114 of the intestinal component 110. The magnetic flaps may be comprised of PTFE, or any other suitable material, and each magnetic flap comprises at least one flat magnet.

Figure 6A:
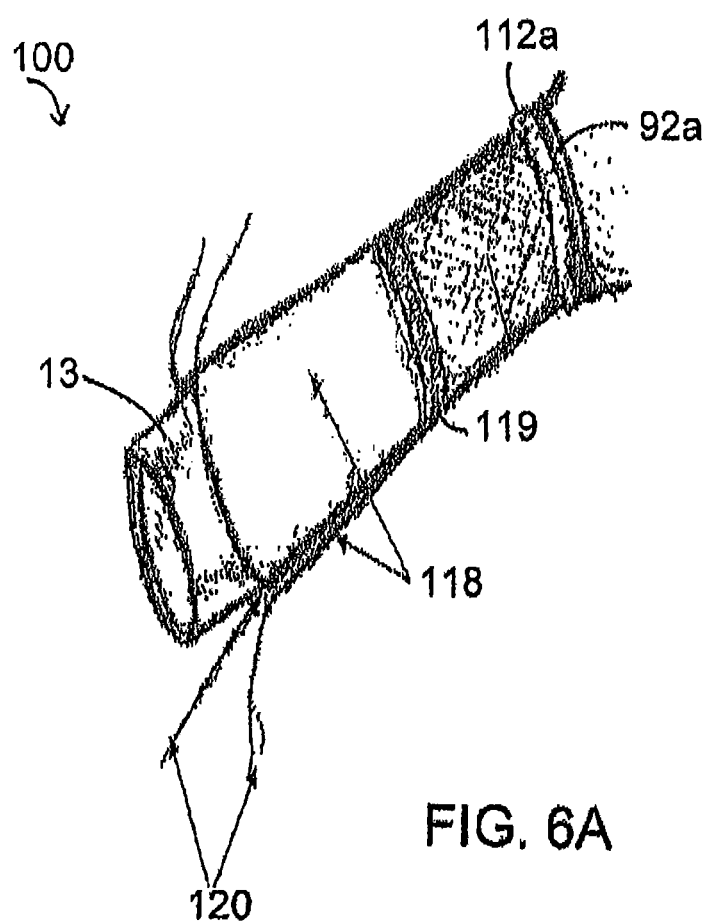
FIGS. 6A and 6B show perspective views of a coupling device being used to form an anastomosis between a jejunum and a stomach.
Figure 6B:
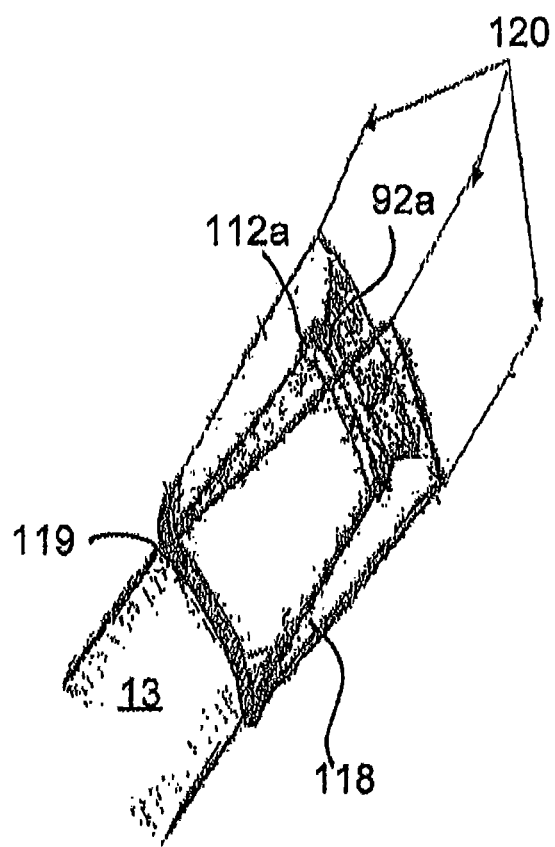

Each of the magnetic flaps is capable of moving between an extended position and a folded position. As shown in FIG. 6A, the magnetic flaps are in the extended position when the flaps extend distally from the second open end 113 of the intestinal component 110, in a direction opposite of the first open end 112 of the intestinal component 110. Alternatively, FIG. 6B shows the intestinal component 110 with the magnetic flaps positioned in the folded position. In the folded position, the magnetic flaps are folded back over the crease ring 119 (in the direction of the first open end 112) such that the magnetic flaps are disposed immediately adjacent to the body 114 of the intestinal component 110. Accordingly, the magnetic flaps of the hemi-stent cover 118 are capable of folding at least about 180° relative to the body 114 of the intestinal component 110. Further, each of the flat magnets of the hemi-stent cover 118 is polarized such that the flat magnets are magnetically biased toward the body 114 of the intestinal component 110 and the body 94 of the gastric component 90. In this manner, the magnetic flaps of the hemi-stent cover 118 are capable of magnetically engaging the body 114 and securing thereto. The magnetic interaction between the gastric component 90 and the hemi-stent cover 118 will be discussed in more detail below.

The magnetic flaps of the hemi-stent cover 118 can comprise any shape so long as the flaps are capable of folding back over the crease ring 119 and magnetically engaging the body 114 of the intestinal component 110. In the embodiments illustrated in FIGS. 6A and 6B, each of the magnetic flaps comprises a flat, rectangular shape such that when the magnetic flaps are folded back over the crease ring 119 and coupled with the body 114 of the intestinal component 110, each of the magnetic flaps can easily conform to the cylindrical shape of the intestinal component 110 and any intestine housed therein. To facilitate the movement of the magnetic flaps of the hemi-stent cover 118 from the extended position to the folded position, one or more filaments 120 may be coupled with the distal ends of each of the magnetic flaps. The filaments 120 may comprise any material known in the art, including suture or biological material that will degrade over a period of time. In this embodiment, the magnetic flaps of the hemi-stent cover 118 can be manipulated between the extended and folded positions simply by moving the filaments 120. Such filaments 120 are especially useful when the coupling device 100 is delivered laparoscopically.

Referring back to FIG. 4B, the first open end 112 of the intestinal component 110 is shown. Similar to the first open end 92 of the gastric component 90, the first open end 112 of the intestinal component 110 comprises a magnetic ring 112a having a perimeter 116 and a plurality of barbs 117 extending radially therefrom. The magnetic ring 112a comprises any ferromagnetic material known in the art so long as the material is capable of magnetically engaging through tissue. In addition, the magnetic ring 112a of the intestinal component 110 may be flexible, semi-flexible or articulated.

The configuration of the magnetic ring 112a is of a sufficient size and shape that a portion of the small intestine is capable of extending therethrough without being overly constricted. Further, the magnetic ring 112a of the intestinal component 110 is configured such that the magnetic ring 112a matches at least a portion of the shape of the magnetic ring 92a of the gastric component 90. In this manner, the magnetic rings 92a, 112a of the gastric component 90 and the intestinal component 110 can be inserted into a body cavity laparoscopically and used to secure the gastric portion of an anastomosis with the intestinal portion of the anastomosis through magnetic engagement. For example, in at least one embodiment, the magnetic rings 92a, 112a both comprise a circular shape as shown in FIGS. 5A and 5B.

Figure 7:
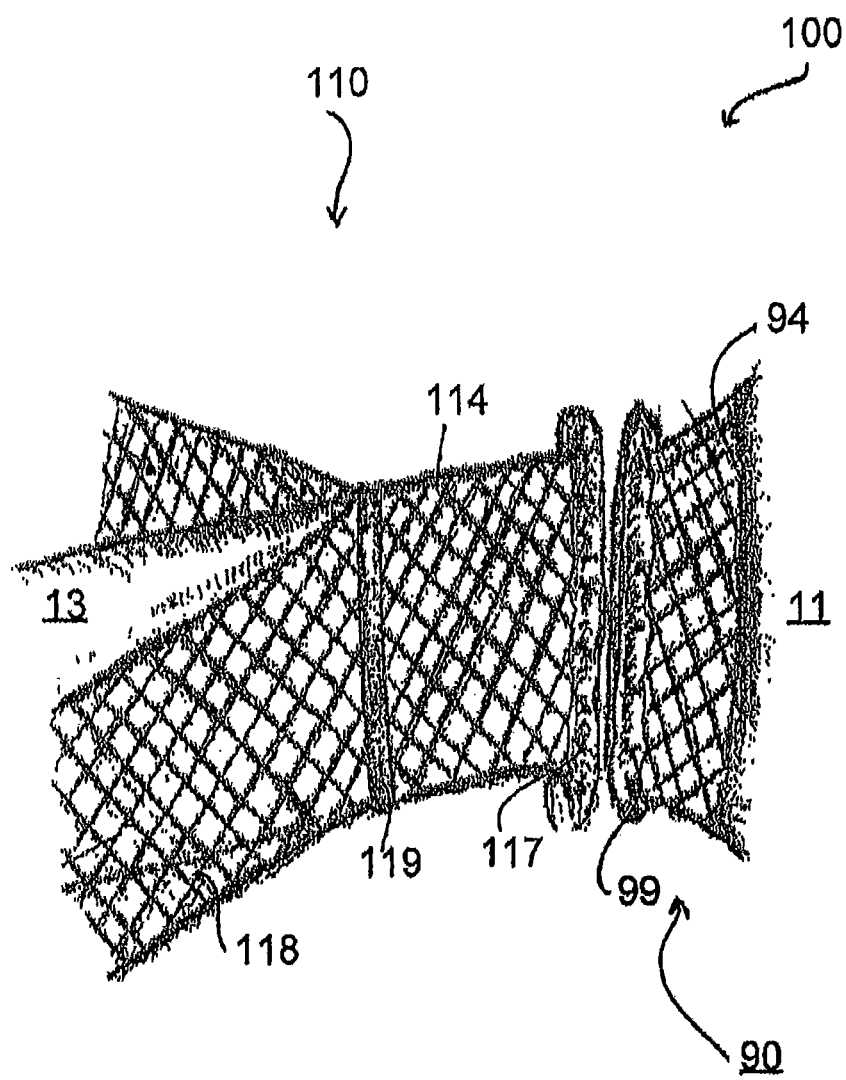
FIG. 7 shows a side view of the intestinal component shown in FIG. 4B applied to a jejunum.

FIG. 7 shows the intestinal component 110 applied around the enterotomy site 70 on the jejunum 13. Specifically, the interior 115 of the intestinal component 110 is positioned over the enterotomy site 70 such that the body 114 houses the jejunum 13 therein and the hemi-stent cover 118 extends distally on the sides of the jejunum 13 (FIG. 5D illustrates the beginning stages of application). To secure the intestinal component 110 in place, the edges of tissue surrounding the enterotomy site 70 are pulled over the magnetic ring 112a and attached to the plurality of barbs 117 extending from the magnetic ring's 112a perimeter 116. In this manner, the barbs 117 secure the intestinal component 110 to the jejunum 13 and the jejunum 13 is positioned such that the enterotomy site 70 can be easily lined up with the gastrotomy site 60.

To facilitate a magnetic interaction between the two magnetic rings 92a, 112a, the magnetic ring 112a of the intestinal component 110 comprises a polarity that is opposite the polarity of the magnetic ring of the gastric component 90. Accordingly, the two magnetic rings 92a, 112a are biased towards each other. Due to the similar configuration of the magnetic rings 92a, 112a of the components 90, 110 and the bias between the same, the magnetic rings 92a, 112a are capable of magnetically engaging. When the magnetic rings of the gastric and intestinal components 90, 110 magnetically engage, the two components 90, 110 form a single unit that is secured to any tissue disposed between the two magnetic rings 92a, 112a. In this manner, when the gastric component 90 is applied over the gastrotomy site 60 located in the wall of the small gastric pouch 11 and the intestinal component 110 is applied proximal to the enterotomy site 70 in the jejunum 13, the gastric and intestinal components 90, 110 are capable of forming an anastomosis between the small gastric pouch 11 and the jejunum 13 using only termino-lateral magnetic fixation and without the need for sutures or staples.

Figure 8:
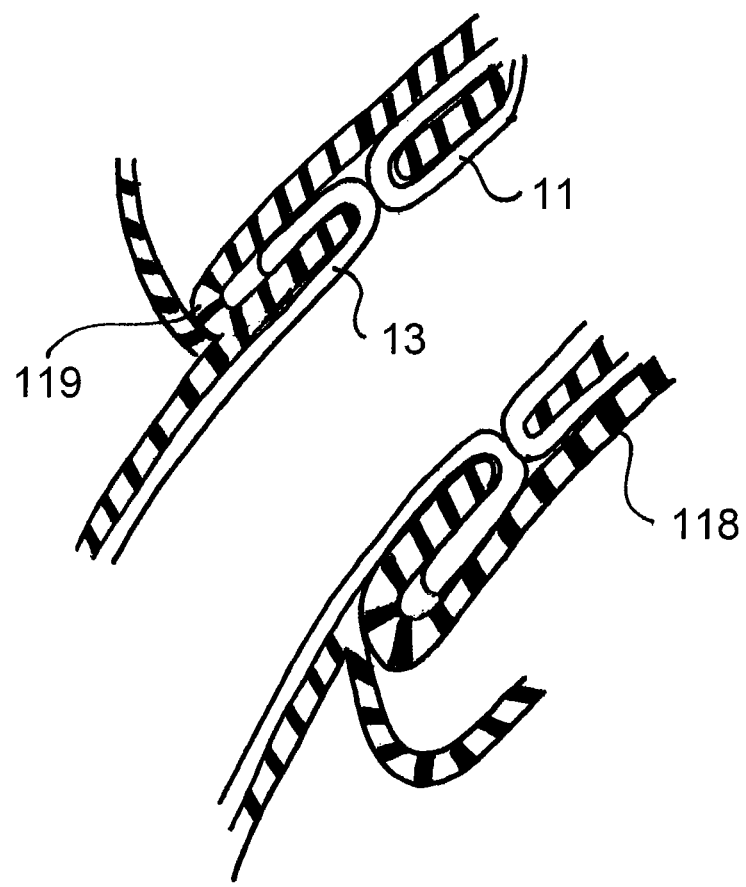
FIG. 8 shows a cross-sectional view of the interaction between the gastric and the intestinal components of the coupling device shown in FIGS. 4A and 4B.
Figure 9:
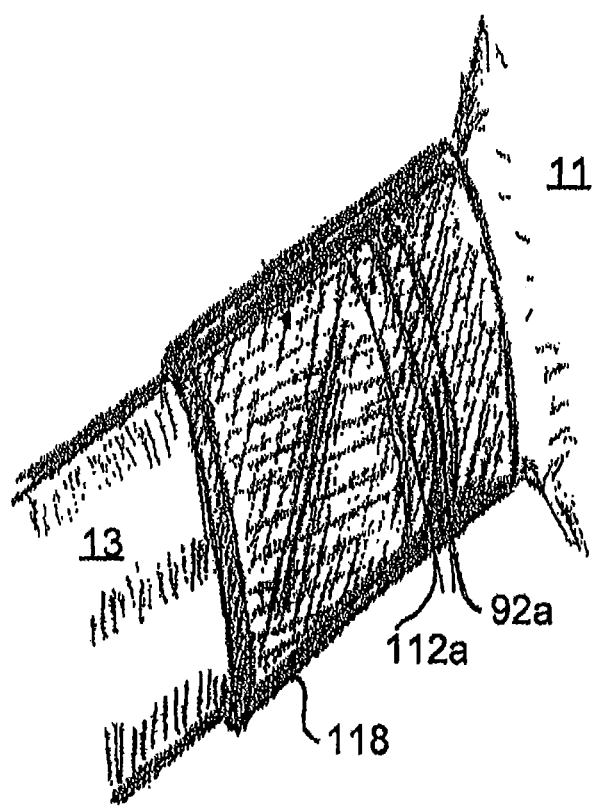
FIG. 9 shows a perspective view of the coupling device of FIG. 8 being used to form an anastomosis between a jejunum and a stomach.
Figure 10:
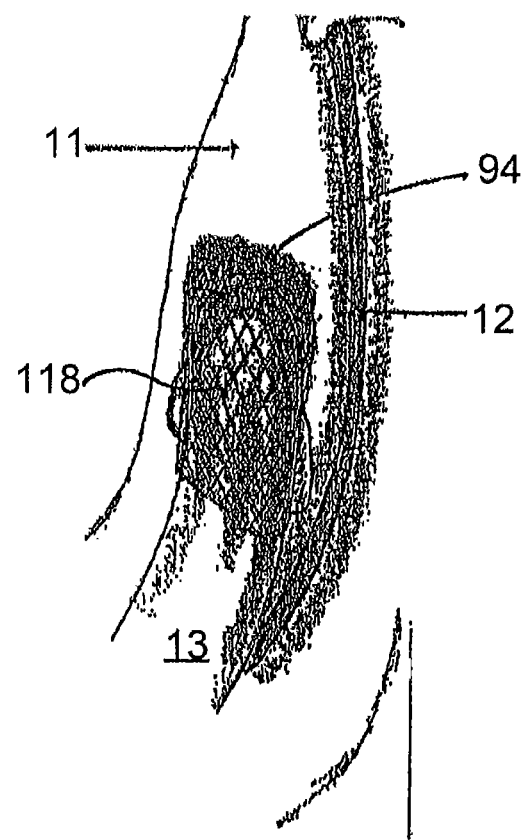
FIG. 10 shows a front view of the coupling device of FIG. 8 being used to form an anastomosis between a jejunum and a stomach.

FIG. 8 shows a cross-sectional view of the intersection between the gastric and intestinal components 90, 110 when the coupling device 100 is used to create an anastomosis between the small gastric pouch 11 and the jejunum 13. As illustrated in FIG. 8, after the magnetic ring 92a of the gastric component 90 is magnetically engaged with the magnetic ring 112a of the intestinal component 110, the magnetic flaps of the hemi-stent cover 118 are moved to the folded position such that the hemi-stent cover 118 provides further magnetic support to the formation of the anastomosis. As previously noted, the at least two magnetic flaps of the hemi-stent cover 118 comprise a length that is greater than the length of the body 114. Accordingly, when the magnetic flaps of the hemi-stent cover 118 are folded toward the first open end 112 of the intestinal component 110 to engage the body 114, the magnetic flaps extend beyond the first open end 112 of the intestinal component 110 as shown in FIGS. 9 and 10. Therefore, when the magnetic rings 92a, 112a of the gastric and intestinal components 90, 110 are magnetically engaged and form an anastomosis between the small gastric pouch 11 and the jejunum 13, the hemi-stent cover 118 extends over the intersection of the two magnetic rings 92a, 112a and magnetically engages a portion of the body 94 of the gastric component 90 in addition to the body 114 of the intestinal component 110. As such, the hemi-stent cover 118 provides additional magnetic support to the anastomosis and reinforces the magnetic interaction between the two components 90, 110.

Figure 11A:
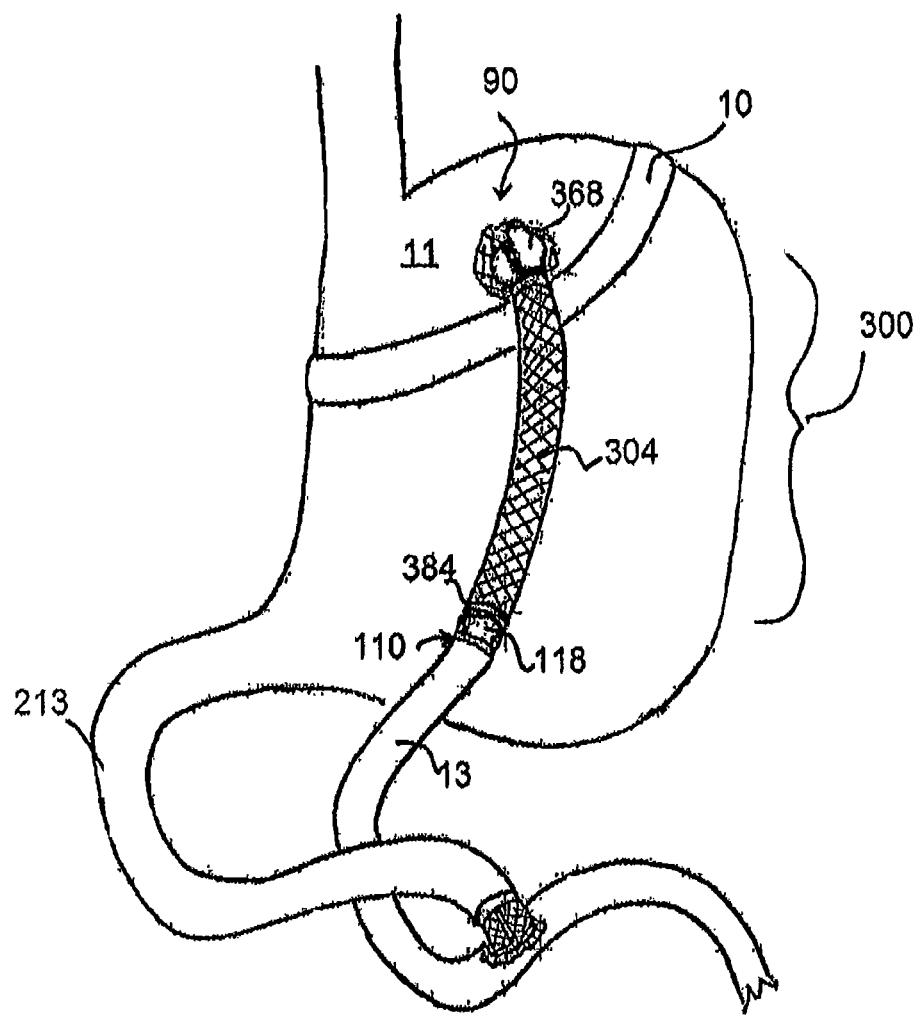
FIGS. 11A and 11B show side views of a stent prosthesis used in conjunction with the coupling device of FIG. 8 to extend the length of the Roux limb.

In one embodiment, the coupling device 100 and/or the gastric remodeling device 10 may be used in conjunction with a stent prosthesis 300 to further prevent tension on the intestines and/or stomach 25 resulting from the RYGBP-E procedure. Now referring to FIGS. 11A and 11B, at least one embodiment of the stent prosthesis 300 is shown. In FIG. 11A, the stent prosthesis 300 is shown coupled with a gastric component 90 and an intestinal component 110 that are applied to the small gastric pouch 11 and the jejunum 13, respectively. Generally, the stent prosthesis 300 may be used to provide an extension such that the gastro jejunum limb (the Roux-limb extending from the small gastric pouch 11 to the jejunum 13) is lengthened and the intestines can remain positioned substantially in their anatomical position within the abdominal cavity. In this manner, the stent prosthesis 300 can reduce the tension on the stomach 25, as well as the jejunum 13 and duodenum 213.

Figure 11B:
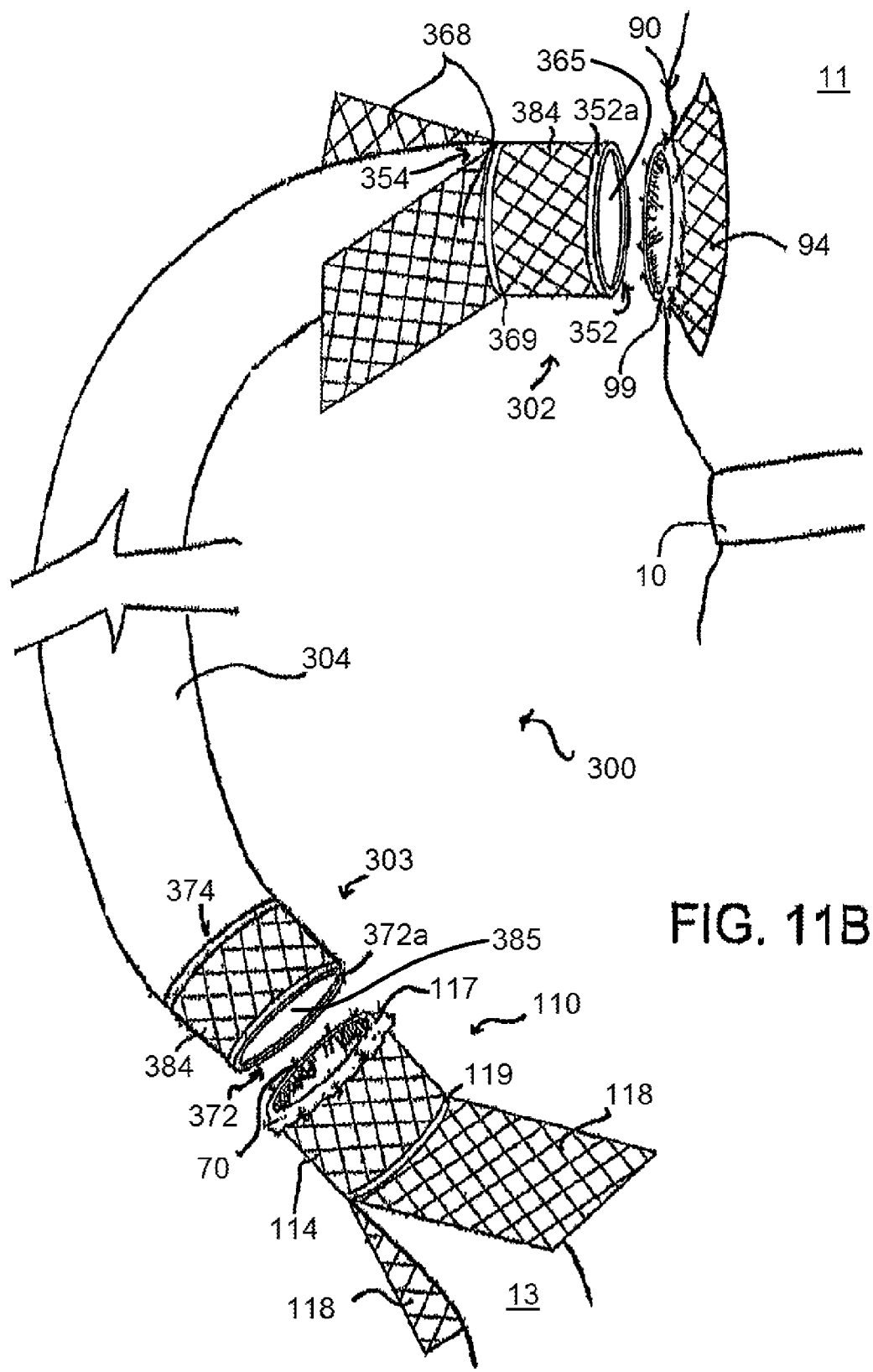
Figure 12:
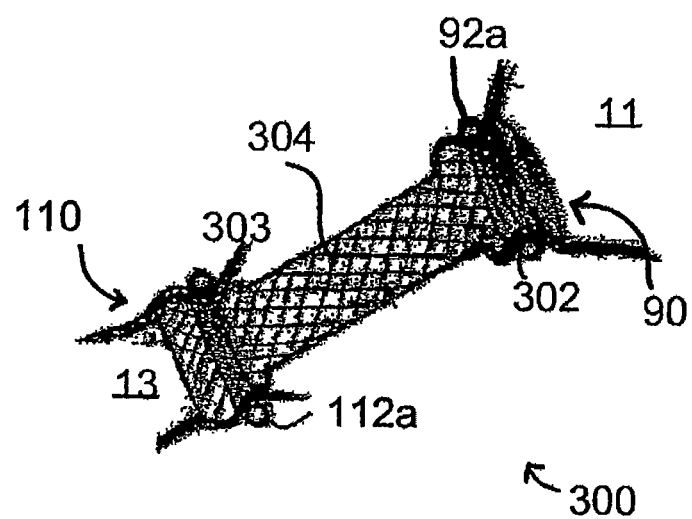
FIG. 12 shows a side view of the stent prosthesis of FIGS. 11A and 11B coupled with the coupling device of FIG. 8.

FIG. 11B shows another view of the stent prosthesis 300, prior to the stent prosthesis 300 being coupled with the small gastric pouch 11 and the jejunum 13. As shown in FIG. 11B, at least one embodiment of the stent prosthesis 300 comprises an elongated tube comprising a first coupling component 302, a second coupling component 303, a body 304, and a hollow interior (not shown) extending between the first and second open ends 302, 303. In this embodiment, the first coupling component 302 is configured similarly to the intestinal component 110 of FIG. 4B and the second coupling component 303 is configured similarly to the gastric component 90 of FIG. 4A. For example, the first coupling component 302 of the stent prosthesis 300 comprises a first open end 352, a second open end 354, a body 364, a hollow interior 365 that extends between the first open end 352 and the second open end, a crease ring 369, and a hemi-stent cover 368. The second open end 354 of the first coupling component 302 is coupled with the body 304 of the stent prosthesis 300 such that the interior 306 of the stent prosthesis is in communication with the interior 365 of the first coupling component 302.

The body 364 of the first coupling component 302 comprises an elongated tube extending between the first open end 352 and the second open end 354. The body 364 may be flexible, comprise any length and, in at least one embodiment, is comprised of PTFE. Furthermore, the body 364 of the first coupling component 302 of the stent prosthesis 300 comprises at least one magnet. For example, and without limitation, the body 364 may comprise a plurality of magnets arranged in a mesh-like configuration or, alternatively, the body 364 may comprise two or more magnets extending between the first open end 352 and the second open end 354.

The first open end 352 of the first coupling component 302 comprises a magnetic ring 352a configured to magnetically engage the magnetic ring 92a of the gastric component 90. The magnetic ring 352a comprises any ferromagnetic material known in the art so long as the material is capable of magnetically engaging through tissue. In addition, the magnetic ring 352a of the first coupling component 302 may be flexible, semi-flexible or articulated. The magnetic ring 352a of the stent prosthesis 300 and the magnetic ring 92a of the gastric component 90 are biased to magnetically engage when the magnetic rings 352a, 92a are in proximity to each other. Accordingly, the first coupling component 302 can magnetically engage a gastric component 90 positioned around a gastrotomy site 60 formed on the wall of the small gastric pouch 11 such that the gastrotomy site 60 and the interior of the stent prosthesis 300 are in communication with each other.

The second open end 354 of the first coupling component 302 comprises a crease ring 369. The crease ring 369 may comprise PTFE or any other material that allows the hemi-stent cover 368 to fold over the area. In addition, the crease ring 369 may be comprised of polyurethane or plastic, and is often comprised of the same material as the body 364. The crease ring 369 functions to form a crease over which the hemi-stent cover 368 can fold when the hemi-stent cover 368 is moved into the folded position.

The hemi-stent cover 368 is coupled with crease ring 369 along the perimeter of the second open end 354 of the first coupling component 302 and extends distally therefrom. The hemi-stent cover 368 comprises at least two magnetic flaps, each of the magnetic flaps having a length greater than the length of the body 364 of the first coupling component 302. The magnetic flaps may be comprised of PTFE or any other suitable material, and each magnetic flap comprises at least one flat magnet.

As described with respect to the hemi-stent cover 118 of the intestinal component 110, each of the magnetic flaps is capable of moving between an extended position and a folded position. The magnetic flaps of the hemi-stent cover 368 are in the extended position when the flaps extend distally from the second open end 354 of the first coupling component 302. Further, the magnetic flaps are in the folded position when the flaps are folded back over the crease ring 369 (in the direction of the first open end 352) such that the magnetic flaps are disposed immediately adjacent to the body 364 of the first coupling component 302. Accordingly, the magnetic flaps of the hemi-stent cover 368 are capable of folding at least about 180° relative to the body 364 of the first coupling component 302.

Each of the flat magnets of the hemi-stent cover 368 is polarized such that the flat magnets are magnetically biased toward the body 364 of the first coupling component 302 and the body 94 of the gastric component 90. In this manner, when the hemi-stent cover 368 is in the folded position, the magnetic flaps of the hemi-stent cover 368 are capable of magnetically engaging the body 364 of the first coupling component 302, as well as the body 94 of the gastric component 90 when the first coupling component 302 and the gastric component 90 are in proximity and magnetically engaged. As described with respect to the hemi-stent cover 118 of the intestinal component 110, when the magnetic rings 352a, 92a of the first coupling component 302 and the gastric component 90 are magnetically engaged, the magnetic flaps of the hemi-stent cover 368 are thereafter moved to the folded position such that the hemi-stent cover 368 engages with the body 364 of the first coupling component 302 and the body 94 of the gastric component 90. In this manner, the hemi-stent cover 368 provides further magnetic support to the connection between the stent prosthesis 300 and the gastric component 90.

The magnetic flaps of the hemi-stent cover 368 can comprise any shape so long as the flaps are capable of folding back over the crease ring 369 and magnetically engaging the body 364 of the first coupling component 302. For example, and without limitation, each of the magnetic flaps may comprise a flat, rectangular shape such that when the magnetic flaps are folded back over the crease ring 369 and coupled with the body 364 of the first coupling component 302, each of the magnetic flaps can easily conform to the cylindrical shape of the first coupling component 302. To facilitate the movement of the magnetic flaps of the hemi-stent cover 368 from the extended position to the folded position, one or more filaments (not shown) may be coupled with the distal ends of each of the magnetic flaps, as described with respect to the intestinal component 110.

The second coupling component 303 of the stent prosthesis 300 is comprised similarly to the gastric component 90 of the coupling device 100. The second coupling component 303 comprises a stent having a first open end 372, a second open end 374, a body 384, and a hollow interior 385 that extends between the first open end 372 and the second open end 374 and is in communication with the interior of the body 304.

The second open end 374 of the second coupling component 303 is coupled with the body 304 of the stent prosthesis 300. The body 384 of the second coupling component 303 extends between the first open end 372 and the second open end 374 of the second coupling component 303 and comprises a flexible material. In addition, the body 384 of the second coupling component 303 comprises at least one magnet disposed therein. For example, the body 384 may comprise a plurality of magnets arranged in a mesh-like configuration, or one or more magnets positioned on opposite sides of the body 384 and extending between the first open end 372 and the second open end 374.

The first open end 372 of the second coupling component 303 comprises a magnetic ring 372a comprised of any ferromagnetic material and is configured in any shape so long as magnetic ring 372a is capable of magnetically engaging the magnetic ring 112a of the intestinal component 112 through a tissue. Further, the magnetic ring 372a may be flexible, semi-flexible or articulated.

The magnetic ring 372a of second coupling component 303 the stent prosthesis 300 is biased such that the magnetic ring 372a can magnetically engage the magnetic ring 112a of the intestinal component 110 when the magnetic rings 352a, 112a are in proximity. Accordingly, the second coupling component 303 can magnetically engage an intestinal component 110 positioned around an enterotomy site 70 formed on the jejunum 13 such that the enterotomy site 70 and the interior of the stent prosthesis 300 are in communication with each other. Further, due to the magnetic polarity of the body 384 as described above, when the hemi-stent cover 118 of the intestinal component 110 is positioned in the folded position, the hemi-stent cover 118 is biased to magnetically engage at least a portion of the body 384 of the second coupling component 303 and, thus, provide further magnetic support to the junction therebetween.

Figure 13:
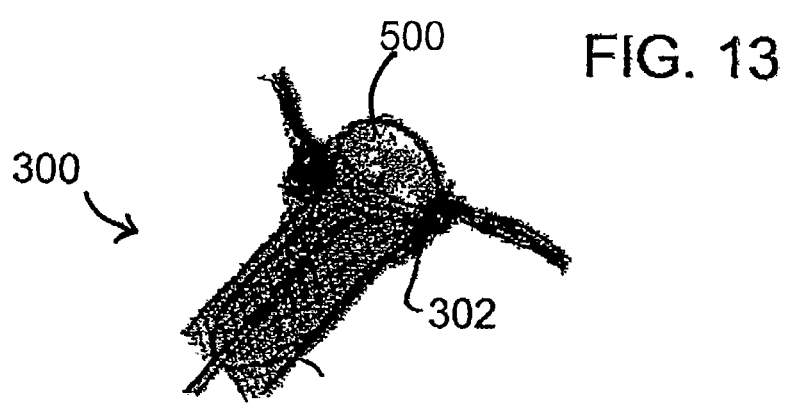
FIG. 13 shows a balloon catheter being used to deliver and secure the stent prosthesis of FIG. 11.

In operation, when it is desired to extend the length of the gastro jejunum limb, the stent prosthesis 300 may be inserted into the body cavity laparoscopically. Optionally, the stent prosthesis 300 may be deployed using a catheter balloon 500 as shown in FIG. 13 to prevent the stent prosthesis 300 from becoming tangled or misconfigured during the course of delivery.

After the stent prosthesis 300 has been delivered into the abdominal cavity, the first coupling component 302 of the stent prosthesis 300 is magnetically coupled with a gastric component 90 that has been previously applied around a gastrotomy site 60 on a small gastric pouch 11 as described herein. Specifically, the magnetic ring 352a of the first coupling component 302 is magnetically engaged with the magnetic ring 92a of the gastric component. Thereafter, the hemi-stent cover 368 is moved into the folded position such that the magnetic flaps engage the body 364 of the first coupling component 302 and a portion of the body 94 of the gastric component 90. Further, when the hemi-stent cover 368 is in the folded position, the magnetic flaps overlap the intersection between the first coupling component 302 and the gastric component 90 and thereby provide further magnetic support to the junction between the gastric component 90 and the stent prosthesis 300.

Similar steps are repeated for the second coupling component 303 of the stent prosthesis 300 and the intestinal component 110 of the coupling device 100. The second coupling component 303 of the stent prosthesis 300 is magnetically coupled with the magnetic ring 112a of an intestinal component 110 that has previously been applied to a portion of divided jejunum 13 as described herein. Further, the hemistent cover 118 of the intestinal component 110 is moved to the folded position, and thereby engages the bodies 114, 384 of the intestinal component 110 and the second coupling component 303 of the stent prosthesis 300. In this manner, the stent prosthesis 300 forms an elongated anastomosis between the small gastric pouch 11 and the jejunum 13, such that the rerouted jejunum is afforded some slack and is thus allowed to remain in a more anatomically-correct position within the abdomen. Accordingly, the application of the stent prosthesis 300 prevents the formation of tension between the stomach 25 and the intestines when a RYGBP-E procedure is preformed.

It will be appreciated that the application of the stent prosthesis 300 is not limited to use in conjunction with the coupling device 100 or the gastric remodeling device 10, and that the stent prosthesis 300 may be used with conventional procedures to prevent tension between various organs such as the stomach and intestines. Accordingly, instead of the stent prosthesis 300 comprising the first and second coupling components 302, 303, the stent prosthesis 300 may be configured to couple with a gastrotomy and/or enterotomy through the use of sutures, staples, or other devices and/or methods that are conventionally known. Further, it will be understood that the stent prosthesis 300 may be used to form an anastomosis between any organs or vessels, especially in such cases where the formation of tension between the effected organs and vessels is particularly problematic.

Further, it will be understood that various embodiments of the stent prosthesis 300 may be used to extend the length Roux limb such that tension is prevented in the intestines and stomach. For example, in at least one embodiment shown in FIGS. 14A and 14B, the body 304 of the stent prosthesis 300 comprises two or more components that magnetically couple together to form a single channel. As shown in FIG. 14B, the two components may be coupled via components similar to the first and second coupling components 302, 303 described herein, and may further comprise a plurality of barbs 390 to assist in securing the junction. This configuration of the stent prosthesis 300 enables a clinician to customize the length of the stent prosthesis 300 to a particular patient during a procedure and, as such, ensure that the proper length is provided.

A user of the gastric remodeling device 10, the coupling device 100, and/or the stent prosthesis 300 (e.g., a physician) may select specific permanent magnets to comprise the various magnetic components of the devices 10, 100, 300 such that the magnetically engaging components exert an optimal amount of magnetostatic force to promote the stabilization of the respective device. For the theoretical application of the gastric remodeling device 10 and the coupling device 100 to the stomach of obese persons, an example calculation is provided below.

Consider the two parallel magnetic rings 92a, 112a shown in FIG. 7. The Maxwell's stress tensor can be written as follows:

$$T_{ij} = \frac{1}{\mu}\left[B_i B_j - \frac{1}{2}B^2 \delta_{ij}\right] \quad [1]$$

Since only $\vec{B}_z$ exits in this application, the Maxwell's stress tensor is written as:

$$T_{ij} = \begin{bmatrix} -\frac{|B_z|^2}{2\mu} & 0 & 0 \\ 0 & -\frac{|B_z|^2}{2\mu} & 0 \\ 0 & 0 & \frac{|B_z|^2}{2\mu} \end{bmatrix} \quad [2]$$

The stress tensor vector which is normal to the surface in two-dimensional coordinates has the form:

$$P = \begin{bmatrix} -\frac{|B_z|^2}{2\mu} & 0 & 0 \\ 0 & -\frac{|B_z|^2}{2\mu} & 0 \\ 0 & 0 & \frac{|B_z|^2}{2\mu} \end{bmatrix} \begin{pmatrix} 0 \\ 0 \\ n_z \end{pmatrix} = \frac{|B_z|^2}{2\mu} \quad [3]$$

where, if $|B_z|=0.5$ T, the pressure is calculated as follows:

$$P = \frac{|B_z|^2}{2\mu} = \frac{0.5^2}{8\pi \times 10^{-7}} = 99.47(\text{kPa}) \quad [4]$$

If it is assumed that the angle between the magnetic field B and normal direction of the magnetic plate is taken as 15°, and area=$[2\pi \times (1.0 \times 10^{-2})] \times (0.5 \times 10^{-2})$ m$^2$ (illustrated in FIG. 1), the force is calculated as follows:

$$F = P \times \sin 30° \times \text{area} = 99.47 \times 0.5 \times \pi \times 0.1 = 15.62 \text{ (Newton)} \quad [5]$$

The force determined by Equation 5 represents the tangential force required to oppose or resist movement or migration magnetic rings 92a, 112a of the coupling device 100. However, optimal forces for each of the magnetic devices described herein, as well as different geometries can be determined using the above-listed equations. Accordingly, the devices 10, 100 disclosed herein can be designed to yield a required force. The geometries of the devices 10, 100 may also be appropriately designed to spread out the force in order to minimize (or maximize) the compression of the tissue. Other forces may be similarly determined for different geometries and areas under consideration.

As described herein, the gastric remodeling device 10 can be used in conjunction with the coupling device 100 to treat obesity. Using the gastric remodeling device 10 and the coupling device 100 described herein allows for a reversible procedure, does not require sutures or staples which may lead to dehiscence or fistula formation, or produce the degree of regurgitation and vomiting observed in conventional methods for the treatment of obesity. Moreover, each of the devices described herein may be inserted into the body cavity laparoscopically, thereby decreasing the stress associated with the procedure and the patient's recovery time. It will be recognized by one of skill in the art that any of the devices described herein may be employed in combination with the other conventional bariatric procedures.

FIGS. 15A-15F show various steps of a method 200 for performing a RYGBP-E procedure. In at least one embodiment of the method 200, the RYGBP-E procedure is easily reversible and does not require any sutures or staples. For ease of understanding, the steps of method 200 will be discussed relative to the gastric remodeling device 10 and the coupling device 100 shown in FIGS. 1A-10, but it will be appreciated that any such devices or systems can be used to perform this method so long as such devices or systems are capable of executing the necessary steps.

Primarily, at step 202, the stomach 25 is divided as into a small gastric pouch 11 and a lower gastric portion. This may be accomplished through the use of the gastric remodeling device 10 as described herein or through any other method. In the embodiment shown in FIG. 15A, the gastric remodeling device 10 is applied to the stomach 25 such that the small gastric pouch 11 is formed. Specifically, the first and second magnetic bars 12, 14 are applied over the anterior and posterior walls of the stomach 25, respectively, and thereafter allowed to magnetically engage each other through the stomach tissue. In this manner, the magnetic bars 12, 14 cause the anterior and posterior walls of the stomach 25 to collapse inwardly, such that the walls are sandwiched between the first and second magnetic bars 12, 14 and the small gastric pouch 11 is formed proximal to the fundus of the stomach 25. After the small gastric pouch 11 is formed, a gastrotomy is performed in the wall of the small gastric pouch 11 as is known in the art.

Figure 15A:
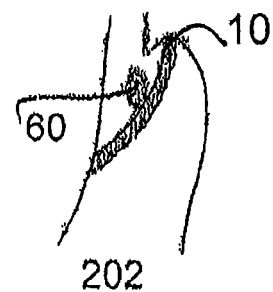
FIGS. 15A-15F illustrate the various steps of a method for performing a reversible RYGBP-E procedure.
Figure 15B:
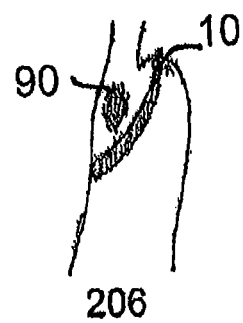
Figure 15C:
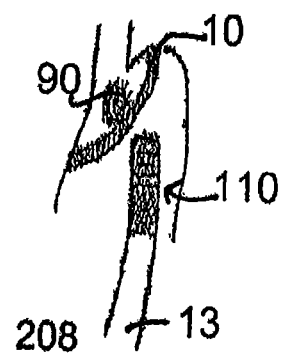

Thereafter, at step 204 and as shown in FIG. 15B, the gastric component 90 is applied around the gastrotomy site 60. In at least one embodiment, the interior 95 of the gastric component 90 is positioned over the gastrotomy site 60 such that the body 94 of the gastric component 90 extends around the gastrotomy site 60 and the interior 95 is in communication with the interior of the small gastric pouch 11. After the gastric component 90 is positioned sufficiently with respect to the gastrotomy site 60, the gastric tissue is coupled with the magnetic ring 92*a* through the use of the plurality of barbs 99 extending from the perimeter 96 of the magnetic ring 92*a*. In at least one embodiment, to secure the gastric component 90 in place, the edges of the tissue surrounding the gastrotomy site 60 are pulled through the interior 95 of the gastric component 60 and the first open end 92, over the magnetic ring 92*a*, and attached to the plurality of barbs 99. Due to the configuration of the barbs 99, the barbs 99 easily pierce the tissue and thereafter retain the gastric tissue securely thereon.

At step 206, an enterotomy is performed on the small intestine just distally of the duodenum 213 such that the small intestine is completely divided between the duodenum 213 and the jejunum 13. As the small intestine comprises a flexible, hollow tube, it will be appreciated that when this type of enterotomy is performed, two enterotomy sites will be created—a first enterotomy site 70 on the jejunum 13 and a second enterotomy site 170 on the duodenum 213. Accordingly, the jejunum 13 is wholly divided from the duodenum 213 and the intestinal component 110 is applied around the enterotomy site 70 on the jejunum 13.

As previously described, the interior 115 of the intestinal component 110 is positioned over the enterotomy site 70 on the jejunum 13 such that jejunum 13 extends through the interior 115 and second open end 113 of the intestinal component 110. The intestinal component 110 is secured to the jejunum 13 in a similar fashion as is described herein with respect to the gastric component 90 and the exterior wall of the stomach 25. Specifically, after the intestinal component 110 is positioned sufficiently with respect to the enterotomy site 70, the edges of the jejuno tissue surrounding the enterotomy site 70 are pulled over the magnetic ring 112*a* and attached to the plurality of barbs 117 extending from the perimeter 116 of the magnetic ring 112*a*. In this manner, the barbs 117 function to secure the intestinal component 110 to the jejunum 13 and the jejunum 13 is positioned such that the enterotomy site 70 can be easily lined up with the gastrotomy site 60 on the small gastric pouch 11.

Figure 15D:
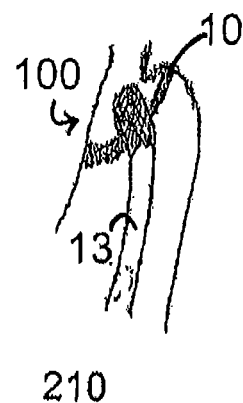

After both the gastric component 90 and the intestinal component 110 are secured around the gastrotomy site 60 and the enterotomy site 70, respectively, the intestinal component 110—and therefore the jejunum 13 coupled therewith—are maneuvered such that the magnetic ring 112*a* of the intestinal component 110 magnetically engages the magnetic ring 92*a* of the gastric component 90 at step 208 (see FIG. 15D). Thereafter, the magnetic flaps of the hemi-stent cover 118 are folded back toward the first open end 112 of the intestinal component 110 and magnetically engage the body 114 of the intestinal component 110 and the body 94 of the gastric component 90. In this manner, the hemi-stent cover 118 provides additional magnetic support to the magnetic engagement of the magnetic rings 92*a*, 112*a* of the gastric and intestinal components 90, 110. Accordingly, a secure anastomosis is formed without the use of sutures or staples, but through magnetic fixation, such that the small gastric pouch 11 is coupled with the jejunum 13 and thus comprises an outlet. This outlet from the small gastric pouch 11 empties directly into the lower portion of the jejunum 13, thus bypassing caloric absorption.

Figure 15E:
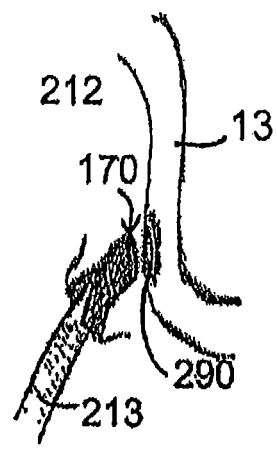
Figure 15F:
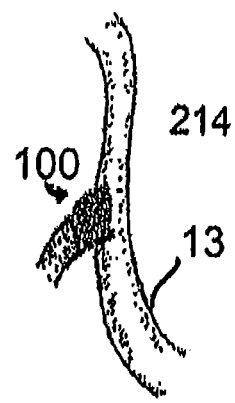

Once the "Roux limb" has been created at step 208, the method 200 proceeds to steps 210 and 212. At step 210, a second intestinal component 110 is applied over the enterotomy site 170 on the duodenum 213. In addition, as shown in FIG. 15E, an enterotomy is performed on a portion of the jejunum 13 such that only a small enterotomy site 290 is formed and the jejunum 13 is not completely divided. A second gastric component 90 is also applied to the small enterotomy site 290 as previously described herein. At step 212, the magnetic ring 112*a* of the intestinal component 112 (and thereby the attached duodenum 213) is maneuvered such that the magnetic ring 112*a* magnetically engages the magnetic ring 92*a* of the gastric component 90 positioned around the small enterotomy site 290. In this manner, an enteroanastomosis is formed and any digestive juices or other matter flowing from the stomach 25 through the pylorus is able to flow from the duodenum 213 into the jejunum 13 and continue through the anatomical course of digestion.

Accordingly, the method 200 achieves a RYGBP-E procedure without the use of staples or sutures and thereby prevents the negative side effects associated with such procedures. Further, because the gastric remodeling device 10 and the coupling device 100 function primarily due to magnetic force, the procedure is reversible. Consider, for example, the case of a once-obese patient who, as a result of undergoing the procedure described herein, is down to a healthy weight. Because the devices described herein function based on principles of magnetic fixation, it is possible to reverse the procedure and thus allow the patient's gastrointestinal tract to resume normal gastric function.

Figure 16:
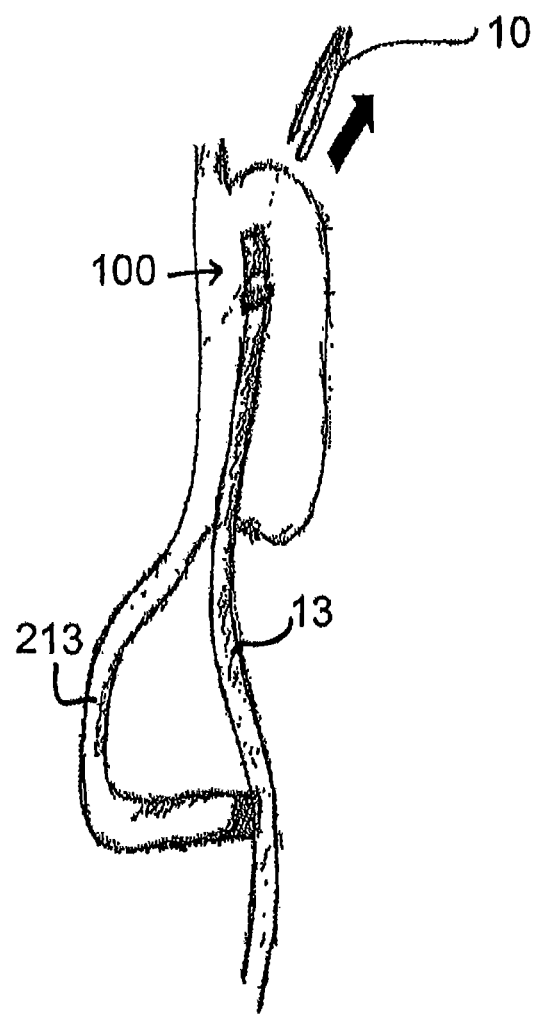
FIG. 16 illustrates a step in a method for reversing the RYGBP-E procedure illustrated in FIGS. 15A-15F.

As illustrated in FIG. 16, this reversion can be achieved simply by removing the first and second magnetic bars 12, 14 of the gastric remodeling device 10 from the anterior and posterior surfaces of the stomach 25, thereby allowing the stomach 25 to return to its anatomical shape. Furthermore, the intestinal component 110 coupled with the jejunal limb may also be occluded to prevent digested matter from bypassing the duodenum 213. In at least one embodiment, the occlusion of the jejunal limb is achieved by applying a laparoscopic magnetic lip of the jejuno at the level of the anastomosis. Alternatively, an endoscopic valve occlusion device (not shown) may be positioned on the jejunum 13 just distally of the anastomosis such that it prevents any matter from flowing therethrough. It will be understood that any other devices or methods may be used to occlude the jejunal limb, including, without limitation, the application of staples to the portion of the jejunum 13 proximate to the anastomosis to constrict and occlude the unnatural outlet from the stomach 25.

The removal of the gastric remodeling device 10 from the stomach 25 and occluding the gastric-jejuno anastomosis allows the patient to gain back the use of their full stomach. Accordingly, the only portion of the gastrointestinal tract that cannot be recovered is the jejunal limb between the gastric anastomosis and the enteroanastomosis where the duodenum 213 reconnects with the jejunum 13, which is of less anatomical significance.

While various embodiments of devices, systems, and methods for accessing performing a RYGBP-E procedure have been described in considerable detail herein, the embodiments are merely offered by way of non-limiting examples of the disclosure. Many variations and modifications will be apparent to one of ordinary skill in the art in light of this disclosure. It will therefore be understood by those skilled in the art that various changes and modifications may be made, and equivalents may be substituted for elements thereof, without departing from the scope of the disclosure. Indeed, this disclosure is not intended to be exhaustive or limiting with respect to scope. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that the disclosure will include, and this description and the appended claims will encompass, all modifications and changes apparent to those of ordinary skill in the art based on this disclosure.

The invention claimed is:

1. A system for reducing the medically effective volume of a stomach and bypassing a duodenum from the digestion of ingested matter, the system comprising:
   an apparatus for restricting the medically effective volume of the stomach comprising a magnetic bar, the magnetic bar for placement around a gastric wall and configured to create a first stomach portion and a second stomach portion, the first stomach portion for primary digestion of ingested food; and
   a first coupling device for bypassing the duodenum comprising:
      a first magnetic component, the first magnetic component for placement around a gastrotomy site on the first stomach portion, wherein the first magnetic component comprises:
         a first open end comprising a first magnetic a perimeter and a plurality of barbs extending radially from the perimeter;
         a second open end; and
         a body extending between the first open end and the second open end, the body comprising at least one magnet;
      wherein the body and the second open end are capable of conforming to an exterior of the first stomach portion and the plurality of barbs are configured to puncture the first stomach portion; and
      a second magnetic component, the second magnetic component for placement around a first enterotomy site on a jejunum, wherein the second magnetic component comprises:
         a first open end comprising a second magnetic ring having a perimeter and a plurality of barbs extending radially from the perimeter;
         a second open end comprising a joint;
         a body having a first length and comprising at least one magnet, the body extending between the first open end and the second open end of the second magnetic component and defining a hollow interior; and
         a stent cover coupled with the joint of the second open end of the second magnetic component and comprising at least one magnetic flap, each of the at least one magnetic flaps comprising a second length and capable of moving relative to the joint between an extended position and a folded position;
         wherein the plurality of barbs of the second magnetic ring are configured to puncture the jejunum, the at least one magnetic flap of the stent cover is configured to magnetically engage the body of the second magnetic component and at least a portion of the body of the first magnetic component when the at least one magnetic flap is in the folded position, and the first and second magnetic rings are configured to magnetically engage each other through the first stomach portion and the jenunum;
      wherein the first and second magnetic components of the first coupling device are configured to magnetically engage each other, hold tissue from the first stomach portion and the jejunum therebetween, and enable communication between the gastrotomy site on the first stomach portion and the first enterotomy site on the jejunum.

2. The system of claim 1, wherein the second length of the at least one magnetic flap is greater than the first length of the body of the second magnetic component.

3. The system of claim 1, wherein the hollow interior of the body of the second magnetic component is configured to receive at least a portion of a second organ therein.

4. The system of claim 1, wherein each of the at least one magnetic flaps comprises at least one flat magnet.

5. The system of claim 1, wherein the system is adapted for laparoscopic delivery.

6. The system of claim 1, wherein each of the at least one magnetic flaps comprises at least one filament extending therefrom.

7. The system of claim 1, wherein the plurality of barbs of the first and second magnetic rings are configured to retain tissue thereon.

8. The system of claim 1, further comprising a second coupling device for coupling the duodenum with a distal portion of the jejunum, the second coupling device comprising:
   a third magnetic component, the third magnetic component for placement around a divided portion of the duodenum; and
   a fourth magnetic component, the fourth magnetic component for placement around a second enterotomy site on a distal portion of the jejunum;
   wherein the third and fourth magnetic components of the second coupling device are configured to magnetically engage each other, hold tissue from the duodenum and the jejunum therebetween, and enable communication between the duodenum and the second enterotomy site on the distal portion of the jejunum.

9. The system of claim 1, further comprising:
a stent for placement between the gastrotomy site on the first stomach portion and the first enterotomy site on the jejunum, the stent comprising a first open end, a second open end, and a body extending between the first open end and the second open end, the body defining a hollow interior, each of the first open end and the second open end comprising a magnetic ring, and the first open end configured to be slidably received within the gastrotomy site and the second open end configured to be slidably received within the first enterotomy site;
wherein the magnetic ring of the first open end of the stent and the first magnetic component of the first coupling device are configured to magnetically engage and hold tissue from the first stomach portion therebetween, and the magnetic ring of the second open end of the stent and the second magnetic component of the first coupling device are configured to magnetically engage each other and hold tissue from the jejunum therebetween.

10. The system of claim 1, further comprising a second coupling device for coupling the duodenum with a distal portion of the jejunum, the second coupling device comprising:
a third component, the third component for placement around a divided portion of the duodenum; and
a fourth component, the fourth component for placement around a second enterotomy site on a distal portion of the jejunum;
wherein the third and fourth components of the second coupling device are configured to engage each other, hold tissue from the duodenum and the jejunum therebetween, and enable communication between the duodenum and the second enterotomy site on the distal portion of the jejunum.

11. The system of claim 1, further comprising:
a stent for placement between the gastrotomy site on the first stomach portion and the first enterotomy site on the jejunum, the stent comprising a first open end, a second open end, and a body extending between the first open end and the second open end, the body defining a hollow interior, each of the first open end and the second open end comprising a ring, and the first open end configured to be slidably received within the gastrotomy site and the second open end configured to be slidably received within the first enterotomy site;
wherein the ring of the first open end of the stent and the first magnetic component of the first coupling device are configured to engage and hold tissue from the first stomach portion therebetween, and the ring of the second open end of the stent and the second component of the first coupling device are configured to engage each other and hold tissue from the jejunum therebetween.

12. A system for reducing the medically effective volume of a stomach and bypassing a duodenum from the digestion of ingested matter, the system comprising:
an apparatus for restricting the medically effective volume of the stomach comprising a bar, the bar for placement around a gastric wall and configured to create a first stomach portion and a second stomach portion, the first stomach portion for primary digestion of ingested food; and
a first coupling device for bypassing the duodenum comprising:
a first component, the first component for placement around a gastrotomy site on the first stomach portion, and
a second magnetic component, the second magnetic component for placement around a first enterotomy site on a jejunum, the second magnetic component comprising:
a first open end,
a second open end comprising a joint,
a body having a first length and comprising at least one magnet, the body extending between the first open end and the second open end and defining a hollow interior, and
a stent cover coupled with the joint of the second open end of the second magnetic component and comprising at least one magnetic flap, each of the at least one magnetic flaps comprising a second length and capable of moving relative to the joint between an extended position and a folded position,
wherein the first component and the second magnetic component of the first coupling device are configured to engage each other, hold tissue from the first stomach portion and the jejunum therebetween, and enable communication between the gastrotomy site on the first stomach portion and the first enterotomy site on the jejunum.

13. A method for treating obesity comprising the steps of:
providing a magnetic bar, the magnetic bar for placement around a gastric wall and configured to create a first stomach portion and a second stomach portion, the first stomach portion for primary digestion of ingested food;
placing the magnetic bar around the gastric wall to result in the first stomach portion comprising an upper portion of the stomach and the second stomach portion comprising a lower portion of the stomach;
providing a first coupling device for bypassing a duodenum from the digestion of ingested matter, the first coupling device comprising:
a first magnetic component, the first magnetic component for placement around a stoma on the first stomach portion; and
a second magnetic component, the second magnetic component for placement around a stoma on a jejunum, the second magnetic component comprising
a first open end,
a second open end comprising a joint,
a body having a first length and comprising at least one magnet, the body extending between the first open end and the second open end and defining a hollow interior, and
a stent cover coupled with the joint of the second open end of the second magnetic component and comprising at least one magnetic flap, each of the at least one magnetic flaps comprising a second length and capable of moving relative to the joint between an extended position and a folded position;
wherein the first and second magnetic components are configured to magnetically engage each other, hold a first tissue and a second tissue therebetween, and enable communication between the stoma on the first stomach portion and the stoma on the jejunum;
attaching the first magnetic component around a stoma on the first stomach portion;
attaching the second magnetic component around the stoma on the jejunum; and magnetically engaging the first magnetic component and the second magnetic component such that the stoma on the first stomach portion and the stoma on the jejunum are in communication with each other.

14. The method of claim 13 further comprising the steps of: providing a second coupling device for coupling the duodenum with a distal portion of the jejunum, the second coupling device comprising:
- a third magnetic component for placement around a stoma of the distal portion on the jejunum, and
- a fourth magnetic component for placement around a stoma on the duodenum,
- wherein the third and fourth magnetic components are configured to magnetically engage each other, hold a third tissue and a fourth tissue therebetween, and enable communication between the stoma on the duodenum and the stoma on the distal portion of the jejunum, wherein the third tissue comprises tissue surrounding the stoma on the distal portion of the jejunum and the forth tissue comprises tissue surrounding the stoma of the duodenum; and
magnetically engaging the third component and the fourth component such that an anastomosis is formed between the stoma on the duodenum and the stoma on the distal portion of the jejunum.

15. The method of claim 13, wherein the first magnetic component of the first coupling device further comprises:
- a first open end comprising a first magnetic ring having a perimeter and a plurality of barbs extending radially from the perimeter,
- a second open end, and
- a body extending between the first open end and the second open end, the body comprising at least one magnet,
- wherein the body and the second open end are capable of conforming to an exterior of the first stomach portion and the plurality of barbs are configured to puncture the first tissue; and
- further comprising the steps of:
  - positioning the second open end of the first magnetic component on the first stomach portion such that the magnetic ring of the first magnetic component is positioned proximal to the first tissue;
  - drawing the first tissue through the first open end of the first magnetic component; and
  - wrapping the first tissue over the first magnetic ring and puncturing the first tissue with the plurality of barbs of the first magnetic ring.

16. The method of claim 15, wherein
the first open end of the second magnetic component comprises a second magnetic ring having a perimeter and a plurality of barbs extending radially from the perimeter,
wherein the plurality of barbs of the second magnetic ring are configured to puncture the second tissue, the at least one magnetic flap of the stent cover is configured to magnetically engage the body of the second magnetic component and the body of the first magnetic component when the at least one magnetic flap is in the folded position, and when the first magnetic ring and the second magnetic ring are in proximity, the first and second magnetic rings are configured to magnetically engage through the first and second tissues, wherein the first tissue comprises gastric tissue surrounding the stoma on the first stomach portion and the second tissue comprises jejunal tissue surrounding the stoma on the jejunum; and
further comprising the steps of: positioning the second open end of the second magnetic component over the stoma on the jejunum such that a portion of the jejunum is housed within the interior of the body of the second magnetic component;
- drawing the second tissue through the interior and the first open end of the second magnetic component;
- wrapping the second tissue over the second magnetic ring and puncturing the second tissue with the plurality of barbs of the second magnetic ring;
- moving the at least one magnetic flap of the stent cover to the folded position; and
- magnetically engaging the body of the first magnetic component and the body of the second magnetic component with the at least one magnetic flap of the stent cover.

17. The method of claim 15, wherein the steps are performed laparoscopically.

18. The method of claim 16, wherein each of the at least one magnetic flaps of the stent cover comprises at least one filament extending therefrom and wherein the step of moving the at least one magnetic flap of the stent cover to the folded position further comprises pulling the at least one filament to maneuver the corresponding at least one magnetic flap into the folded position.

* * * * *